(12) United States Patent  
Presthus et al.

(10) Patent No.: US 7,052,453 B2  
(45) Date of Patent: **\*May 30, 2006**

(54) INCONTINENCE TREATMENT WITH URETHRAL GUIDE

(75) Inventors: James B. Presthus, Edina, MN (US); Timothy G. Dietz, Califon, NJ (US); Stanley Levy, Jr., Saratoga, CA (US); F. Allen House, Pleasanton, CA (US); Steven H. Trebotich, Newark, CA (US); Abdul M. Tayeb, San Leandro, CA (US); Oren A. Mosher, Castro Valley, CA (US); George L. Matlock, Pleasanton, CA (US); Terry E. Spraker, Portola Valley, CA (US)

(73) Assignee: Solorant Medical, Inc., Livermore, CA (US)

( \* ) Notice: Subject to any disclaimer, the term of this patent is extended or adjusted under 35 U.S.C. 154(b) by 60 days.

This patent is subject to a terminal disclaimer.

(21) Appl. No.: 10/301,561

(22) Filed: Nov. 20, 2002

(65) Prior Publication Data

US 2003/0144576 A1    Jul. 31, 2003

Related U.S. Application Data

(63) Continuation-in-part of application No. 09/991,368, filed on Nov. 20, 2001, now Pat. No. 6,685,623.

(51) Int. Cl.  
*A61F 2/00* (2006.01)  
*A61N 1/30* (2006.01)

(52) U.S. Cl. .......................................... 600/29; 604/19
(58) Field of Classification Search ................ 600/29, 600/439, 459, 462, 591; 601/3, 45; 604/22, 604/164.08, 96.05; 606/47, 21, 23, 192, 606/1, 41, 45; 607/101, 113; 482/112, 113, 482/8; 73/379.01; 602/102, 105, 116, 122, 602/156; 74/490.06; 901/29

See application file for complete search history.

(56) References Cited

U.S. PATENT DOCUMENTS

| | | | |
|---|---|---|---|
| 4,742,829 A | | 5/1988 | Law et al. |
| 4,838,506 A | | 6/1989 | Cooper |
| 4,846,818 A | | 7/1989 | Keldahl et al. |
| 4,946,443 A | | 8/1990 | Hauser et al. |
| 5,239,999 A | | 8/1993 | Imran |
| 5,304,214 A | | 4/1994 | DeFord et al. |
| 5,344,435 A | * | 9/1994 | Turner et al. ............... 607/101 |
| 5,370,675 A | * | 12/1994 | Edwards et al. ............ 607/101 |
| 5,385,544 A | * | 1/1995 | Edwards et al. ............ 604/22 |
| 5,433,720 A | | 7/1995 | Faccioli et al. |
| 5,480,417 A | * | 1/1996 | Hascoet et al. ............. 607/101 |

(Continued)

*Primary Examiner*—John P. Lacyk  
(74) *Attorney, Agent, or Firm*—Townsend and Townsend and Crew LLP

(57) ABSTRACT

Devices and methods for aligning a probe body and a treatment surface adjacent a target tissue. A guide shaft can be positioned in a first body orifice. The probe body can be positioned in a second body orifice in a predetermined position relative to the guide so as to position the treatment surface adjacent the target tissue.

83 Claims, 34 Drawing Sheets

U.S. PATENT DOCUMENTS

| | | | |
|---|---|---|---|
| 5,647,868 A * | 7/1997 | Chinn ........................ 606/21 |
| 5,666,954 A * | 9/1997 | Chapelon et al. ........... 600/439 |
| 5,836,314 A | 11/1998 | Benderev et al. |
| 5,848,986 A | 12/1998 | Lundquist et al. |
| 5,995,875 A | 11/1999 | Blewett et al. |
| 6,063,045 A * | 5/2000 | Wax et al. .................. 600/591 |
| 6,071,230 A | 6/2000 | Henalla |
| 6,071,279 A * | 6/2000 | Whayne et al. ............... 606/41 |
| 6,081,749 A | 6/2000 | Ingle et al. |
| 6,091,995 A | 7/2000 | Ingle et al. |
| 6,136,010 A | 10/2000 | Modesitt et al. |
| 6,139,569 A | 10/2000 | Ingle et al. |
| 6,159,170 A | 12/2000 | Borodulin et al. |
| 6,216,704 B1 | 4/2001 | Ingle et al. |
| 6,231,514 B1 * | 5/2001 | Lowe et al. ................. 600/462 |
| 6,236,891 B1 | 5/2001 | Ingle et al. |
| 6,283,987 B1 | 9/2001 | Laird et al. |
| 6,292,700 B1 | 9/2001 | Morrison et al. |
| 6,394,998 B1 * | 5/2002 | Wallace et al. ................. 606/1 |
| 6,506,189 B1 * | 1/2003 | Rittman et al. ............... 606/41 |
| 6,685,623 B1 * | 2/2004 | Presthus et al. .............. 600/29 |
| 2002/0133150 A1 * | 9/2002 | Whayne et al. ............... 606/41 |

* cited by examiner

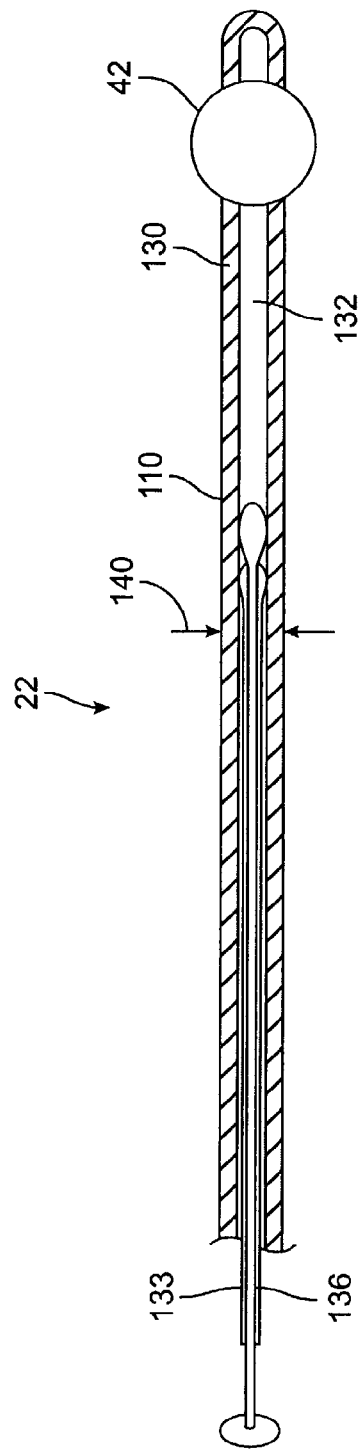
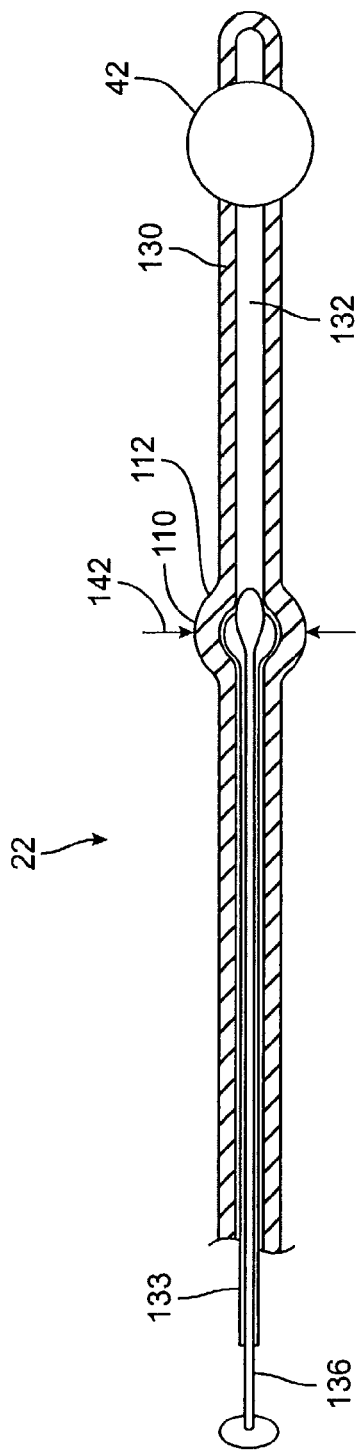
FIG. 18A
FIG. 18B

INCONTINENCE TREATMENT WITH URETHRAL GUIDE

This application is a continuation-in-part of U.S. patent application Ser. No. 09/991,368, filed Nov. 20, 2001 (now U.S. Pat. No. 6,685,623) entitled "Incontinence Treatment with Urethral Guide," the complete disclosure of which is incorporated herein by reference.

BACKGROUND OF THE INVENTION

The present invention relates generally to medical devices methods, systems, and kits. More specifically, the present invention provides devices and methods for positioning a treatment surface adjacent a target tissue to selectively heat and shrink tissues, particularly for the noninvasive treatment of urinary incontinence, hernias, cosmetic surgery, and the like.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external vaginal sphincter, and most often, the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such noninterventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

It has recently been proposed to selectively deliver RF energy to gently heat fascia and other collagenated support tissues to treat incontinence. One problem associated with delivering RF energy to the targeted tissue is the alignment of the electrodes with the target tissue. Direct heating of target tissue is often complicated since the target tissue is offset laterally and separated from the urethra by triangular shaped fascia sheets supporting the urethra. These urethra supporting fascia sheets often contain nerve bundles and other structure that would not benefit from heating. In fact, injury to these nerve bundles may even promote incontinence, instead of providing relief from incontinence.

For these reasons, it would be desirable to provide improved devices, methods, systems, and kits for providing improved alignment devices and methods that would improve the positioning of heating electrodes adjacent the target tissue and away from the surrounding, sensitive nerve bundles.

BRIEF SUMMARY OF THE INVENTION

The present invention provides devices, methods, systems, and kits for positioning a treatment surface adjacent a target tissue. In one embodiment, the present invention can be used for treating urinary incontinence.

Embodiments of the probe and guide of the present invention can accurately position a treatment surface, such as an electrode array, adjacent a target tissue by utilizing the human anatomy to help guide the treatment surface into contact with the target tissue. Generally, the guide can be inserted into a first body orifice and the probe can be inserted into a second body orifice and placed in a predetermined position relative to the guide so as to position the treatment surface adjacent the target tissue in the second body orifice.

In some embodiments, the guide can be inserted into the urethra to help position the treatment surface adjacent the target tissue in the vagina. In the embodiments, the probes can include a probe body comprising a treatment surface. A probe body can be registered with the guide that is positioned in the urethra and positionable in the vagina to help align the treatment surface with a target tissue in the vagina.

In one embodiment, the urethral guide can be physically couplable to the probe body. Optionally, the urethral guide can be removably attached to the probe body and/or rotatably attached to the probe body. The rotatable attachment can provide flexibility in positioning treatment surface adjacent the target tissue. The removable attachment allows the probe body and urethral guide to be independently inserted into the body orifices. After both have been inserted, the two can optionally be attached to align the treatment assembly with the target tissue. Optionally, the probes of the present invention may have a coupling structure on each side of the probe body to provide proper alignment of the treatment surface with target tissue both to the left and right of the non-target urethra tissue.

Some embodiments of the urethral guides of the present invention can be configured to bias the electrodes into the target tissue. Such biasing can improve the efficiency of electrical energy delivery to the target tissue while avoiding energy delivery to the surrounding non-target tissue if the electrodes are not in proper contact with the target tissue.

Some embodiments of the probe body and guide means can be rigid and rigidly connected to each other. The rigid configuration of the probes of the present invention allows the physician to maintain the position of the treatment surface relative to the target tissue. Other embodiments of the probe body and guide, however, can be partly or completely flexible.

In other embodiments, the urethral guide will not be physically coupled to the probe body but will be registered with the probe body through its position relative to the position of the probe body.

In one embodiment, the urethral guide can be registered with or in communication with the probe body based on its physical location relative to the probe body. A palpation member (such as a bump or indentation, landmark, a clip, a marking, or the like) on the urethral guide and the probe body can provide landmarks for the physician to assist the physician in positioning the treatment surface of the probe body adjacent the target tissue.

In another embodiment, the urethral guide can be registered with the probe body through an electromagnetic coupling such as a Radiofrequency (RF) coupling, magnetic coupling, or light sensing coupling (either visible or infrared). In such embodiments, the urethral guide and probe body do not have to be physically coupled with each other (but can be, if desired) and typically can be moved freely, relative to each other.

In one embodiment, the urethral guide and/or the probe body can include one or more RF transmitter(s) and RF sensor(s). The RF coupling can provide a RF position signal to a controller that is indicative of the spacing between the sensors and transmitters on the urethral guide and the probe. The RF signal can be delivered to the controller so that the controller can inform the user of the positioning of the probe body relative to the urethral guide. Once the urethral guide and probe have been placed in their proper positions in the body orifices and in a proper, predetermined position relative to each other, the RF sensor will produce a position signal that informs the controller that the probe is disposed in a position that places the treatment surface adjacent the target tissue.

In another embodiment, a magnetic coupling that includes one or more magnetic field transmitter(s) (e.g., an electromagnet) and/or one or more magnetic field sensors (e.g., Hall Effect sensors) to position the probe body in a proper position relative to the urethral guide. The magnetic coupling can provide an electromagnetic signal that is indicative of the spacing between the urethral guide and the probe. The magnetic field signal can be delivered to the controller through the magnetic field sensors so that the controller can inform the user of the positioning of the probe body. Once the urethral guide and probe have been placed in their proper position in the body orifices and in a proper, predetermined position relative to each other, the magnetic field sensor will produce a signal that indicates a proper positioning of the probe relative to the urethral guide.

In some configurations, the controller can be configured to inform the user that there is an improper or proper spacing between the probe body and urethral guide. In some configurations, the controller can be configured to prevent delivery of energy to the treatment surface until a proper spacing or proper positioning of the treatment surface is achieved. In other configurations, the controller can be configured to provide an indication (such as a readout on a monitor, or an audible signal) that there is a proper positioning of the probe body in the vagina relative to the urethral guide.

The guides of the present invention can also optionally include an expansible member adjacent its distal end. The urethral guide can be moved through the urethra and into the patient's bladder. Once in the bladder, the expansible member can be expanded so as to prevent proximal movement of the urethral guide and probe body.

In some embodiments, the urethral guide can include a temperature sensor that is coupled to the controller to allow the user to monitor the tissue temperature of the urethra.

The methods of the present invention generally comprise positioning a guide in the patient's body and guiding a treatment surface, such as an electrode array to a target tissue. Once the treatment surface is positioned against the target tissue, the target tissue can be treated. In some embodiments, treatments comprise delivering an electrical energy to heat and shrink or stiffen the target tissue.

One embodiment of the method of the present invention comprises placing a guide into a first body orifice (e.g., urethra). A treatment probe having a treatment surface can be inserted into a second body orifice (e.g., vagina). The probe can be placed in a predetermined position relative to the guide (e.g., registered) so as to position the treatment surface in proper alignment with a target tissue in the second body orifice. Thereafter, the target tissue can be treated with the treatment surface In some embodiments, the methods of the present invention can include the step of measuring the length of the patient's urethra. Once the patient's urethra has been measured, the physician can then calculate a predetermined distance of the urethra for advancement of the urethral guide. In one embodiment, the predetermined distance is approximately a mid-urethra point. In other embodiments, however, the predetermined target distance can be other target distances, that are larger or smaller than the mid-urethra point. Locating the midpoint of the urethra can be done automatically or the process of midpoint location can be carried out by manually measuring the length of the patient's urethra and inserting marked positioning devices to a position called for by the measured urethral length.

Once the mid-urethra point is calculated (or other predetermined distance), the urethral guide can be placed in the urethra and advanced to the mid-urethra point to "mark" the mid-urethra. In some embodiments, the mid-urethra point can be marked with the urethral guide by using an RF transmitter, magnetic field transmitter, or a mechanical palpation member that can indicate to the physician the position of the midurethra. Once the mid-urethra point is marked, a variety of methods can be used to position the treatment surface near the marker and adjacent the target tissue. Thereafter, the treatment surface can be used to treat the target tissue.

The present invention further provides kits for treating incontinence. The kits of the present invention typically include any of the probes and guides as described herein. The kits will generally include a package for holding the probe, guide, and instructions for use which describe any of the exemplary methods described herein. Optionally, the kits may include a controller, power source, electrical connections, or the like.

A further understanding of the nature and advantages of the invention will become apparent by reference to the remaining portions of the specification and drawings.

BRIEF DESCRIPTION OF THE DRAWINGS

FIGS. 18A and 18B are cross sectional views of a simplified urethral guide having an expandable portion;

DESCRIPTION OF THE SPECIFIC EMBODIMENTS

The present invention provides methods, devices, systems, and kits for accurately positioning a treatment surface, such as an electrode array, adjacent fascia and other collagenated tissues to selectively treat the target tissue. In a particular embodiment, the present invention accurately directs an electrical current flux through the target tissue between bipolar electrodes that are contacting the target tissue to shrink or stiffen the collagenated tissue.

Exemplary embodiments of the present invention heat target tissue in the vagina for treating urinary incontinence. The urethra is composed of muscle structures that allow it to function as a sphincter controlling the release of urine from the bladder. These muscles are controlled by nerve bundles that in part run in close proximity to the urethra-bladder junction and along the axis of the urethra. Pelvic surgery in this region has been associated with the development of intrinsic sphincter deficiency of the urethra. It is therefore important that any tissue treatment avoid areas containing nerve pathways that supply the urethra. Because the present invention provides accurate placement with the target tissue, collateral damage to surrounding nerve bundles and other organs can be reduced.

While the remaining discussion will be directed at treating incontinence in a female patient, it should be appreciated that the concepts of the present invention are further applicable to other noninvasive and invasive surgical procedures, and are not limited to treating urinary incontinence.

Figure 1A:
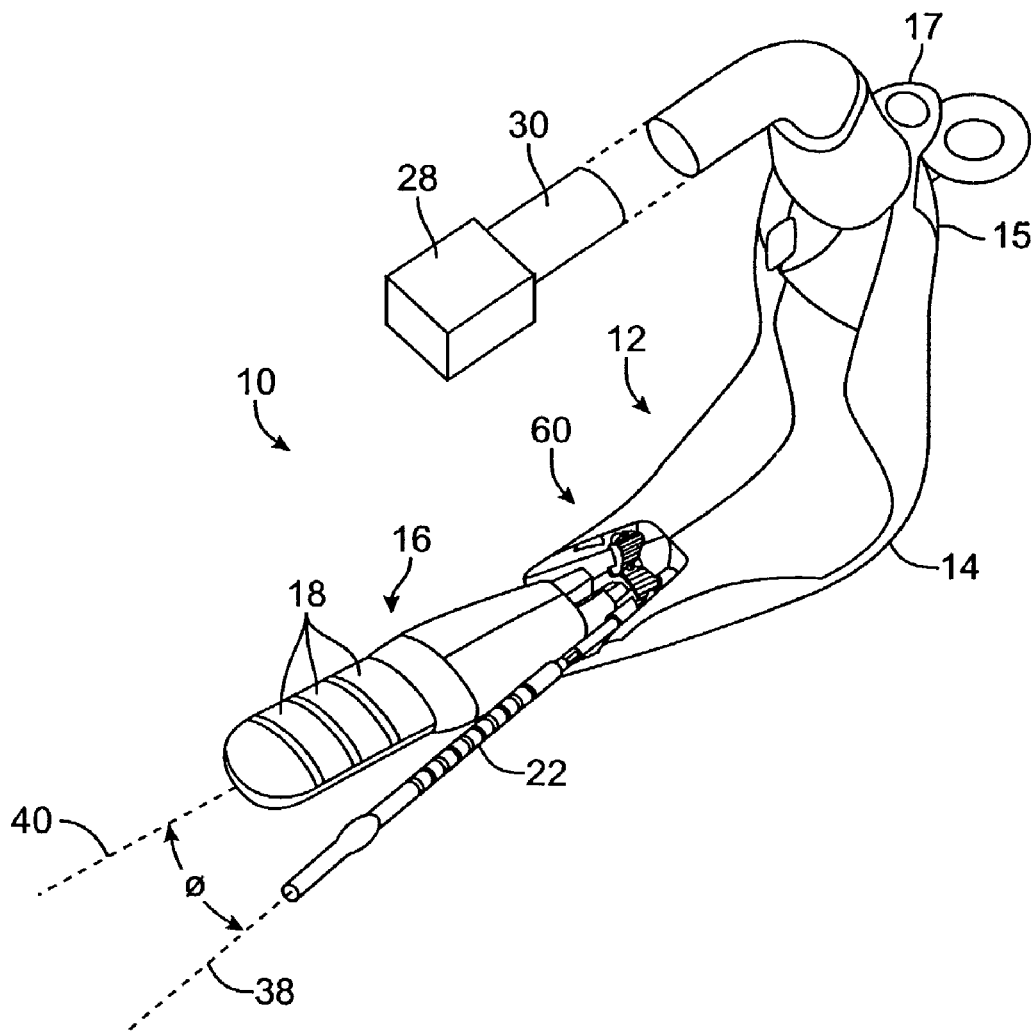
FIG. 1A illustrates an embodiment of an electrosurgical probe of the present invention.

FIG. 1A illustrates an exemplary electrosurgical probe 10 of the present invention. The electrosurgical probe includes an applicator or probe body 12 having a proximal portion 14 and a distal portion 16. Proximal portion 14 of the probe body 12 generally includes a handle 15 and one or more triggers or switches 17 for activating a delivery of electrical energy to the target tissue or for deploying a temperature probe into the target tissue to monitor the tissue temperature during treatment. Distal portion 16 can include a treatment surface 18 that has at least one electrode or other type of treatment assembly. The treatment assembly can include an electrode on a needle, ultrasound transducer, microwave antenna, a needle for delivery of a therapeutic agent, or the like. A guide body or shaft 22 can be attachable to the probe body 12 to assist in the proper positioning of the distal portion 16 of probe body 12 and treatment surface 18 with a target tissue. As will be described in detail below, other embodiments include a guide 22 that is not attached to probe body 12.

Systems of the present invention can further include a power supply 28 that is in electrical communication with the electrode assembly 18 through electrical couplings 30. Optionally, a controller (not shown) may be incorporated into the probe and/or with the power supply to control the delivery of energy to the heating electrodes and to provide visual and audio outputs to the physician. Some exemplary controllers are described in commonly assigned U.S. Pat. No. 6,081,749, the complete disclosure of which is incorporated herein by reference.

Exemplary embodiments of the probes of the present invention are for use in treating incontinence. Such probes will typically be substantially rigid, and sized and shaped to be insertable into a patient's vagina. In such embodiments, the distal portion will have a length between approximately 2 cm and 8 cm, and will have a width or diameter between approximately 1.0 cm and 3.0 cm. The probes can be composed of a plastic (such as polyester polycarbonate, or the like) or an inert metal (such as gold plated brass, or the like), or other bio-compatible materials that are typical of intravaginal devices. It should be appreciated however, that in alternative embodiments, the probes and guides may be partially or completely flexible. For example, in one embodiment, an electrode array may be mounted on a balloon type surface or the electrode array can be built in as features on a flexible printed circuit assembly (e.g., electrodes on flexible plastic film).

Electrodes 18 of the present invention can take a variety of forms. As illustrated in FIG. 1A, the heating electrodes can include a plurality of curved electrodes disposed on the distal portion 16 of probe body 12. In the illustrated embodiment, there are three curved electrodes 18. It should be appreciated however, that any number of electrodes and a variety of shaped electrodes can be used. A more complete description of various types of electrodes that can be used with the devices and methods of the present invention are shown and described in commonly assigned U.S. Pat. No. 6,091,995, the complete disclosure of which is incorporated herein by reference.

Figure 2:
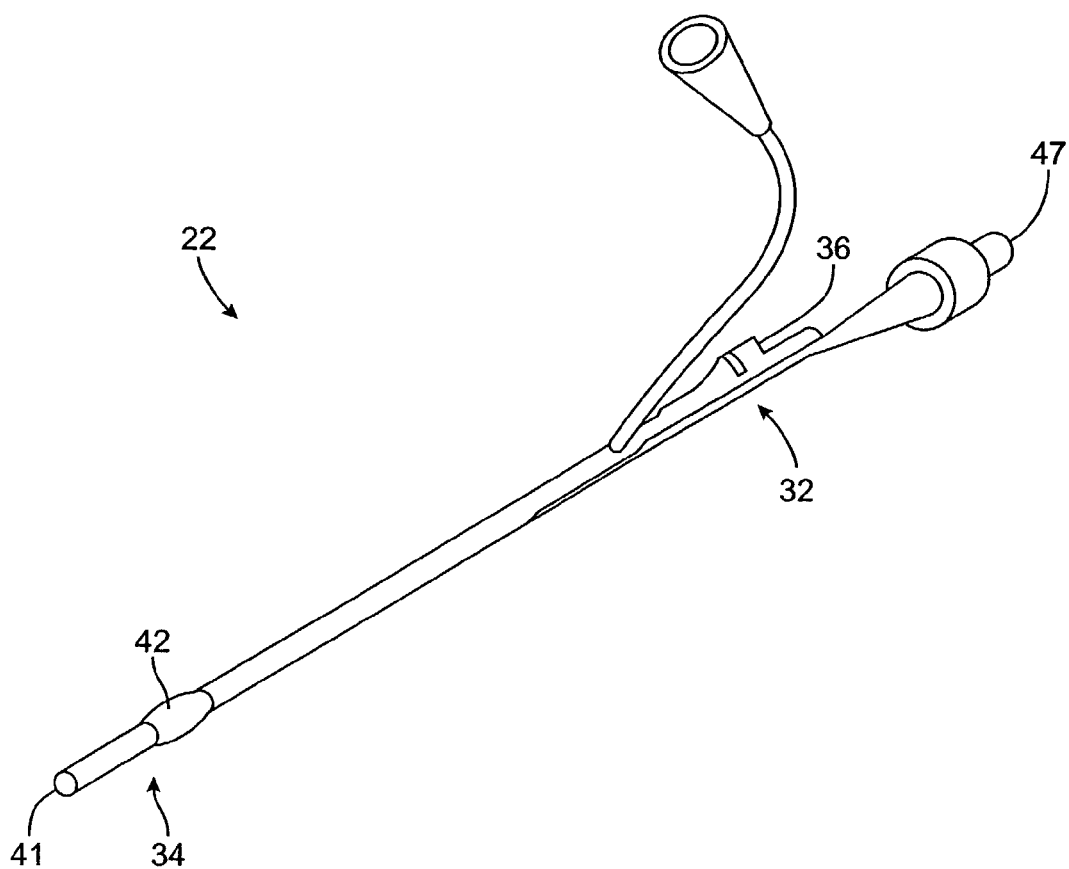
FIG. 2 illustrates an embodiment of an urethral guide shaft of the present invention.

FIG. 2 illustrates an exemplary embodiment of the guide shaft 22 of the present invention that is couplable to probe body 12. Guide shaft 22 has a proximal portion 32 and a distal portion 34. In one exemplary embodiment, guide shaft 22 of the present invention is removably attached to the probe body 12 to allow for independent placement of the probe 10 and guide shaft 22 in the patient's body. A clamping structure 36, such as a series of serrations, is disposed on the proximal portion 32 to allow the guide 22 to be removably attached to the probe body 12.

While not illustrated, guide 22 can further include a temperature sensor to sense the temperature of the urethra, before, after, and during the heating treatment. Sensors may be a thermocouple, thermistor, fiber optic light based, RTD or other sensors known to those skilled in the art. The temperature sensor can be coupled to the controller to allow monitoring of the temperature of the urethral tissue. In some embodiments, if the urethra is heated beyond a predetermined threshold temperature, the controller can be configured to output a cue to the physician to inform the physician of the measured temperature. Alternatively, upon reaching a threshold temperature, the controller can be configured to stop delivery of heating energy to the electrode array.

Figure 3:
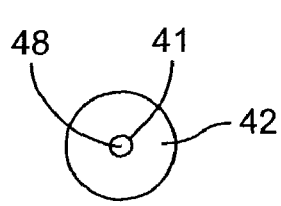
FIG. 3 is a simplified end view of a distal orifice and expansible member disposed on guide shaft.
Figure 4:
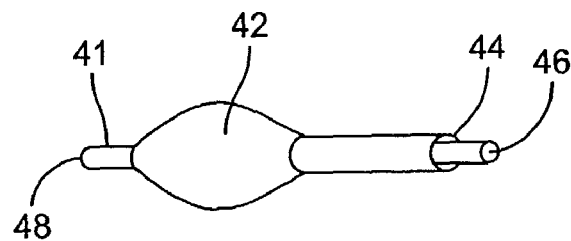
FIG. 4 is a simplified side view of an embodiment of the expansible member.

As illustrated in FIGS. 2–4, guide 22 can optionally include a tip 41 and an expansible member 42 positioned on the distal portion 34 of guide 22. Expansible member 42 can be inflated and deflated via an inflation lumen 44. Guide 22 can also include a fluid lumen 46 that has a proximal orifice 47 and distal orifice 48. In the particular configuration illustrated in FIGS. 3 and 4, the fluid lumen 46 can be coaxial with inflation lumen 44 and disposed through expansible member 42. The fluid lumen 46 can be used to deliver fluids to a body organ or to drain fluid from the body organ. Proximal orifice 47 of the fluid lumen 46 can be coupled to an aspiration or fluid source (not shown) to assist in the transfer of fluid through the fluid lumen 46. In such embodiments, expansible member 42 can be annular shaped and will have a corresponding annular inflation lumen 44 and fluid lumen 46 will be concentric or lateral with each other. It should be appreciated however, that a variety of other configurations of the lumens 44, 46 can be used without departing from the concepts of the present invention.

Figure 5:
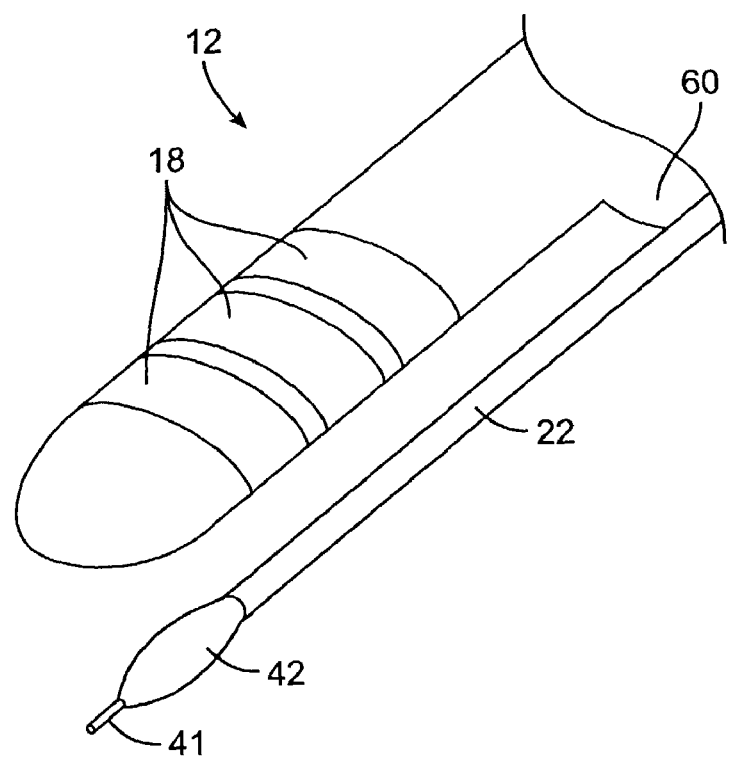
FIG. 5 is a simplified view of an alternative embodiment of the noninvasive probe of the present invention.
Figure 6:
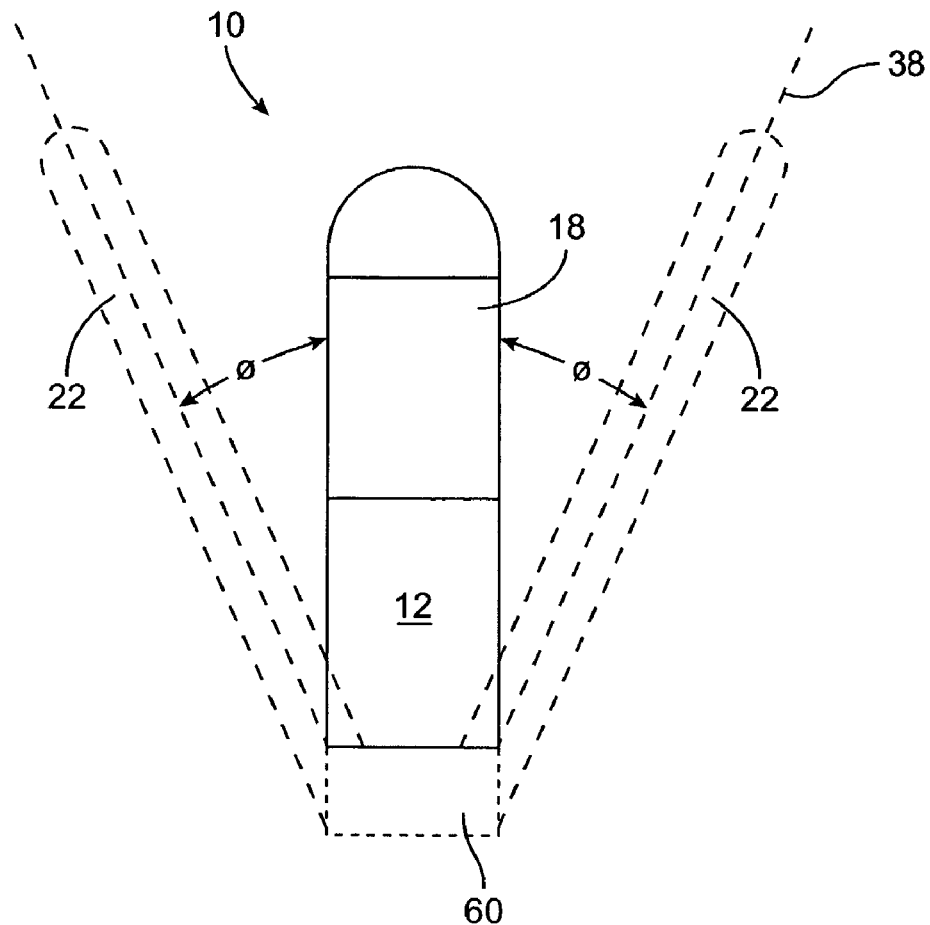
FIG. 6 illustrates an exemplary embodiment of a coupling structure on two sides of the probe body which allows for positioning of the probe body against target tissue on both the left and right side of the urethra.

In some embodiments, urethral guide 22 can be coupled to the probe body 12 in an angled, offset configuration (FIG. 1A). Typically, a longitudinal axis 38 of urethral guide 22 will be angled from a longitudinal axis 40 of the probe body 12 (FIGS. 1A and 6). The angle θ will typically be between approximately 5° degrees and 30° degrees, and preferably approximately between approximately 11° degrees and 15° degrees. It should be appreciated, however, that in alternative embodiments, urethral guide 22 and probe body 12 may be in a parallel configuration (FIG. 5). The angled arrangement is more preferred than the parallel arrangement, because in the angled offset arrangement, as the probe is moved distally through the body orifice, the probe and guide will diverge along the angled path so that the electrodes will be positioned offset from the position of the guide and farther away from the urethra-bladder junction, which extends laterally from a longitudinal axis of the urethra.

In an embodiment most clearly illustrated in FIG. 6, a distal end of urethral guide 22 will also be positionable distal of the distal end 16 of the probe body. Thus, when the expansible member 42 of the guide extends into the bladder B, the electrodes 18 on the probe body 12 will be maintained in a position proximal of the bladder B. Such a configuration can prevent inadvertent delivery of electrical energy to the non-target bladder tissue.

Figure 7:
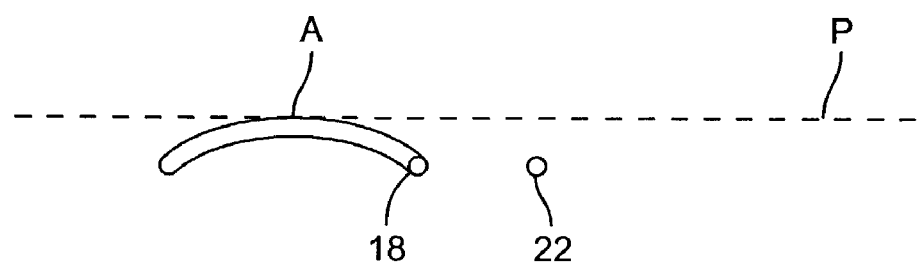
FIG. 7 is a simplified cross sectional view of a radiused electrode and a guide of the present invention illustrating a lateral offset of the guide relative to the probe body and an orthogonal offset relative to a plane of the electrode.

One exemplary configuration of the treatment surface 18 relative to the urethral guide 22 is illustrated schematically in FIG. 7. In such a configuration, the treatment surface 18 includes radiused electrodes that have an apex A. The guide 22 will be offset laterally from an axis of the probe body 12, typically between 5° degrees to 30° degrees, and offset below a plane P that is orthogonal/tangent to the apex A (or parallel to an upper plane of a planar electrode). By offsetting the distal end of the guide 22 below the top plane of the electrode, the guide 22 can tension the vaginal surface tissue engaged by the probe body 12 and bias the electrodes 18 into contact with the target tissue. Such a biasing configuration can improve the delivery of the electrical energy from the electrodes 18 into the target tissue and reduce the chance of delivering energy to non-target tissue.

In one embodiment, guide 22 can be rigidly coupled to probe body 12 with a coupling assembly 60 so as to maintain a rigid assembly. By maintaining a substantially rigid connection, rigid guide 22 can properly position electrodes 18 offset laterally from a sensitive non-target tissue, such as the urethra, so that delivery of electrical energy through the electrodes 18 is sufficiently spaced from the non-target tissue.

In some configurations, the coupling assembly 60 of the present invention can be configured to allow attachment to the probe body along both sides of the probe body. As shown in FIG. 6, urethral guide 22 can be positioned laterally along either the left or right side so as to allow contact of the electrodes 18 with tissue laterally to the left or right of the urethra.

Figure 1B:
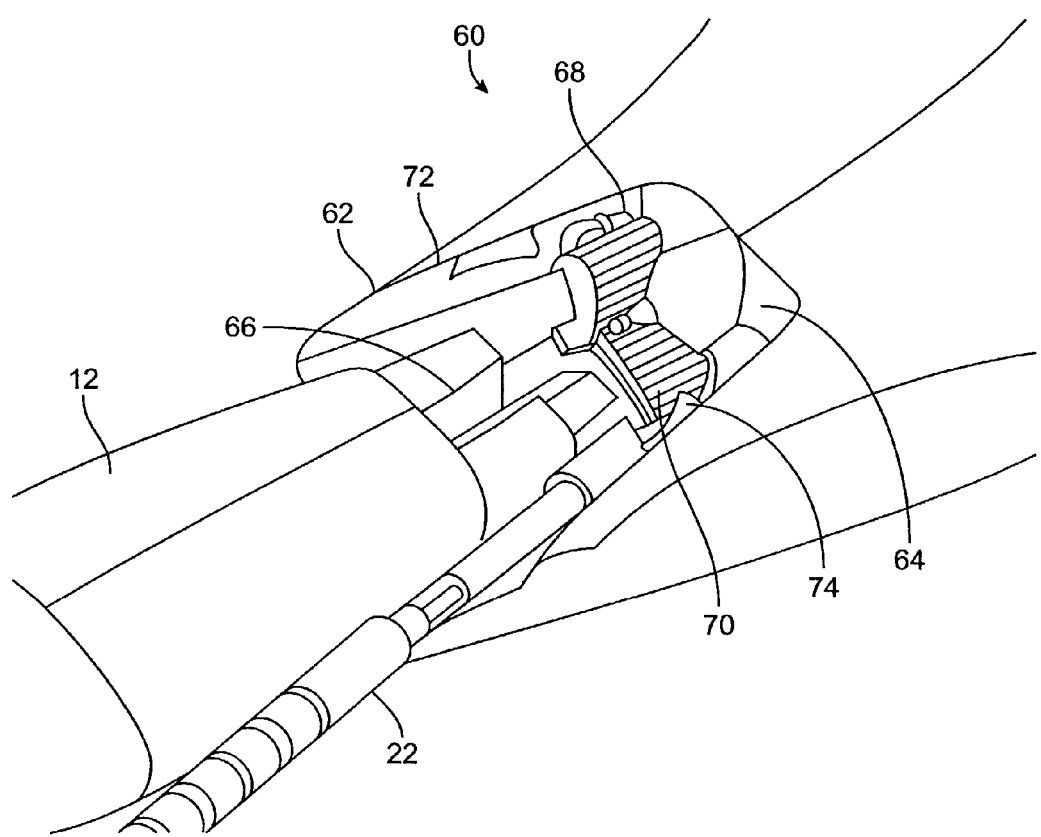
FIG. 1B is a close up perspective view of an exemplary coupling assembly.

The coupling assembly 60 of the present invention can provide an attachment between the guide 22 and the probe body 12 that allows the user to attach and detach the guide to position the electrodes adjacent the target tissue. One exemplary coupling assembly is illustrated in FIG. 1B. The coupling assembly includes a substantially symmetrical left and right pockets 62, 64 that can receive a proximal end of the urethral guide 22. A rotatable guide clip 66 having a left and right coupling handles 68, 70 is disposed between left pocket 62 and right pocket 64. The left pocket 62 and right pocket 64 can include a serrated mount 72 that can interact with clamping structure 36 on the proximal end of the guide 22. Additionally, the pockets 62, 64 can include a snap feature 74 that can interact with the left and right coupling handles 68, 70 to lock the guide 22 within the pockets.

The urethral guide can enter the pockets either by vertically or axially sliding the proximal end of the urethral guide 22 into a selected pocket. In exemplary embodiments, the proximal end of the urethral guide 22 includes matching serrations (not shown) that match the serrated mount 72 in the pocket so as to allow for incremental axial positioning of the urethral guide with respect to the applicator and handle. After the guide 22 is positioned in a desired axial position, the selected handle 68, 70 can be secured by snapping it into the snap feature 74.

Figure 9:
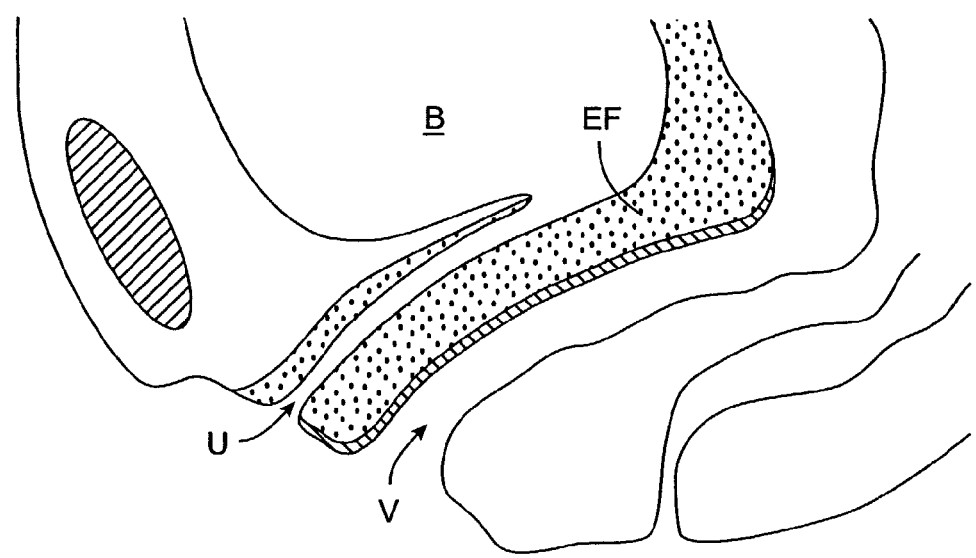
FIG. 9 is a cross sectional view of the tissue that can be targeted for non-invasive treatment using the methods of the present invention.
Figure 9A:
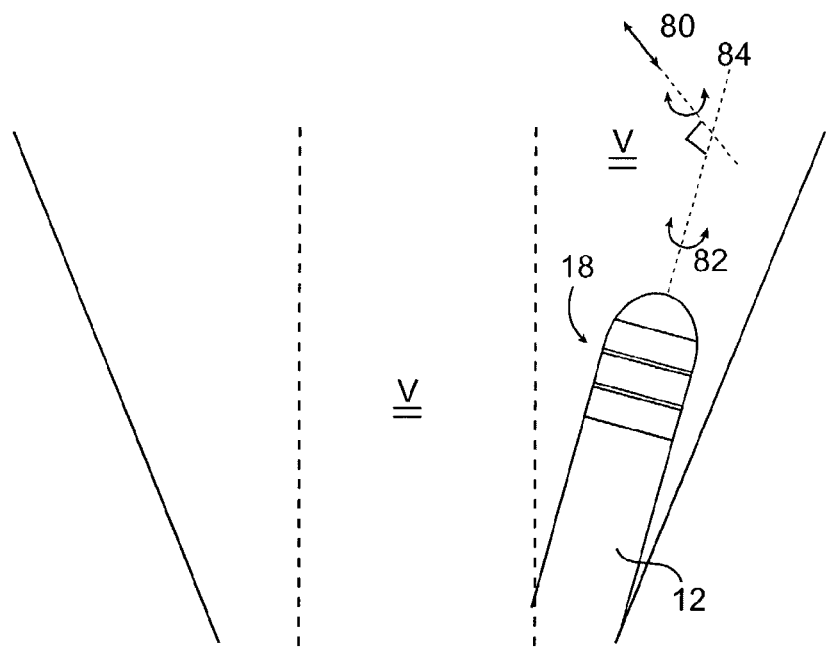
FIGS. 9A–9C illustrate some embodiments that comprise a urethral guide that is rotatably attached to the probe body about at least one axis.
Figure 9B:
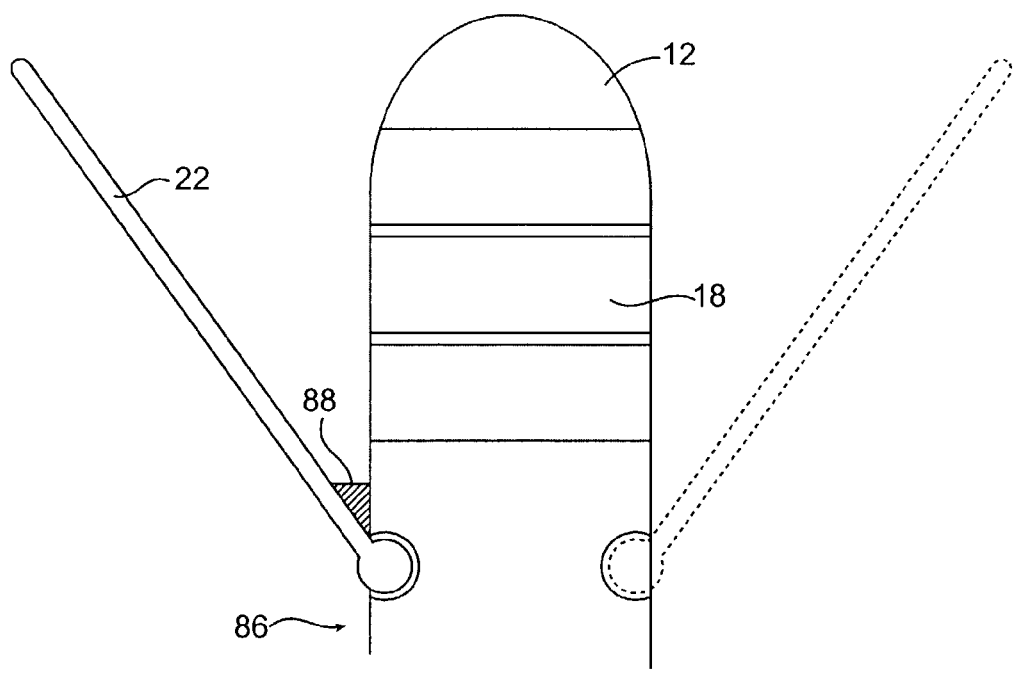
Figure 9C:
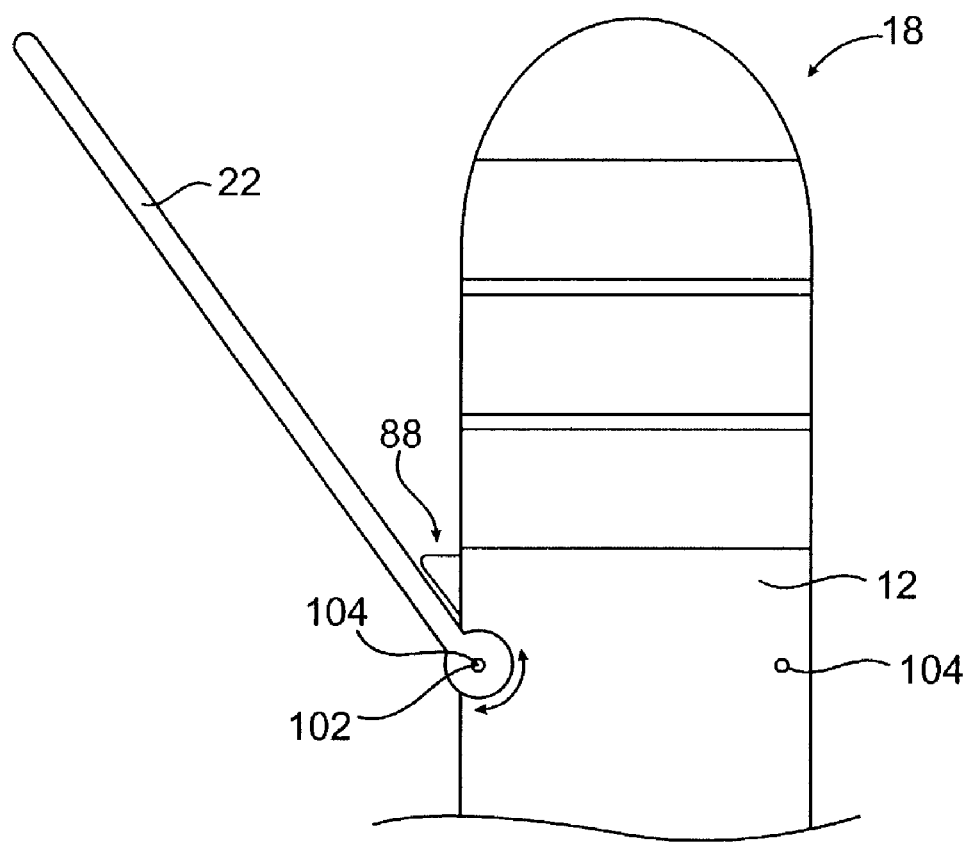

FIGS. 9A to 9C illustrate an embodiment of the probe and urethral guide 22 that allows the operating physician the flexibility of changing the position of the urethral guide 22 relative to the probe body 12. As illustrated in the top view FIG. 9A, it is preferred to position the treatment surface 18 of the applicator in a laterally offset position relative to the urethral tissue U. In one embodiment, the urethral guide can be coupled to probe body 12 in a manner that allows the physician to place the treatment surface in different orientations lateral to the urethra tissue U. As illustrated by the arrows in FIG. 9A, in some embodiments, the treatment surface 18 will be rotatable about one or more axes and/or movable in at least one direction. For example, in one embodiment, the urethral guide can be movable in at least one of an up/down direction 80, rotation about a longitudinal axis of the probe body 82, and rotation about an axis perpendicular to the longitudinal axis 84 (e.g., pivot around a distal portion of the probe body).

In the embodiment illustrated in FIG. 9B, probe body can be coupled to the urethral guide 22 with a ball joint 86 or other joint that allows rotation of the guide about at least some of the degrees of freedom 80, 82, 84. In some configurations, probe body 12 can include a physical stop 88 that limits the pivoting of the urethral guide 22 to prevent the urethral guide from being positioned below a minimum angular offset, (e.g., 11 degrees). Preventing the urethral guide from going below a minimum angular offset can prevent the treatment surface from being aligned with the urethral tissue U and fascia sheets. As illustrated further in FIG. 9B, ball joint 86 can be disposed on the left and/or right side of the probe body 12 so as to allow treatment on the tissue that is laterally to the left and right of the urethral tissue.

The ball joint 86 can be implemented in a variety of ways. For example a proximal end of urethral guide 22 can include a ball, while probe body 12 can include a socket with a cover so as to removably capture and rotatably hold the ball within the socket. In another example the proximal end of urethral guide 22 can include pins or other protrusions that can be retained in a dimple that is in the joint of the probe body 12 so as to rotatably couple the urethral guide to the probe body.

If it is desirable to only pivot the urethral guide 22 about one axis, a simple joint 98 can be used to couple the urethral guide 22 to the probe body 12 so as to allow rotation 100 about a single axis. As can be appreciated, there are a variety of conventional methods of rotatably attaching the urethral guide 22 to the probe body 12. In the illustrated example in FIG. 9C, urethral guide 22 includes a hole 102 that can mate with a pin 104 on the probe body 12. In such embodiments, the urethral guide can be removable or non-removable and the urethral guide 22 can be attached to the left and/or right side of the probe body 12.

It should be appreciated however, that other conventional attachment means can be used to attach the urethral guide 22 to the probe body 12. For example, the guide 22 and probe body 12 can be coupled with a threaded attachment, a toggle clamp mechanism for pressing a clamping surface of the guide against the probe body, a sliding latch mechanism clip, a ¼ turn fastener, or the like.

Figure 8:
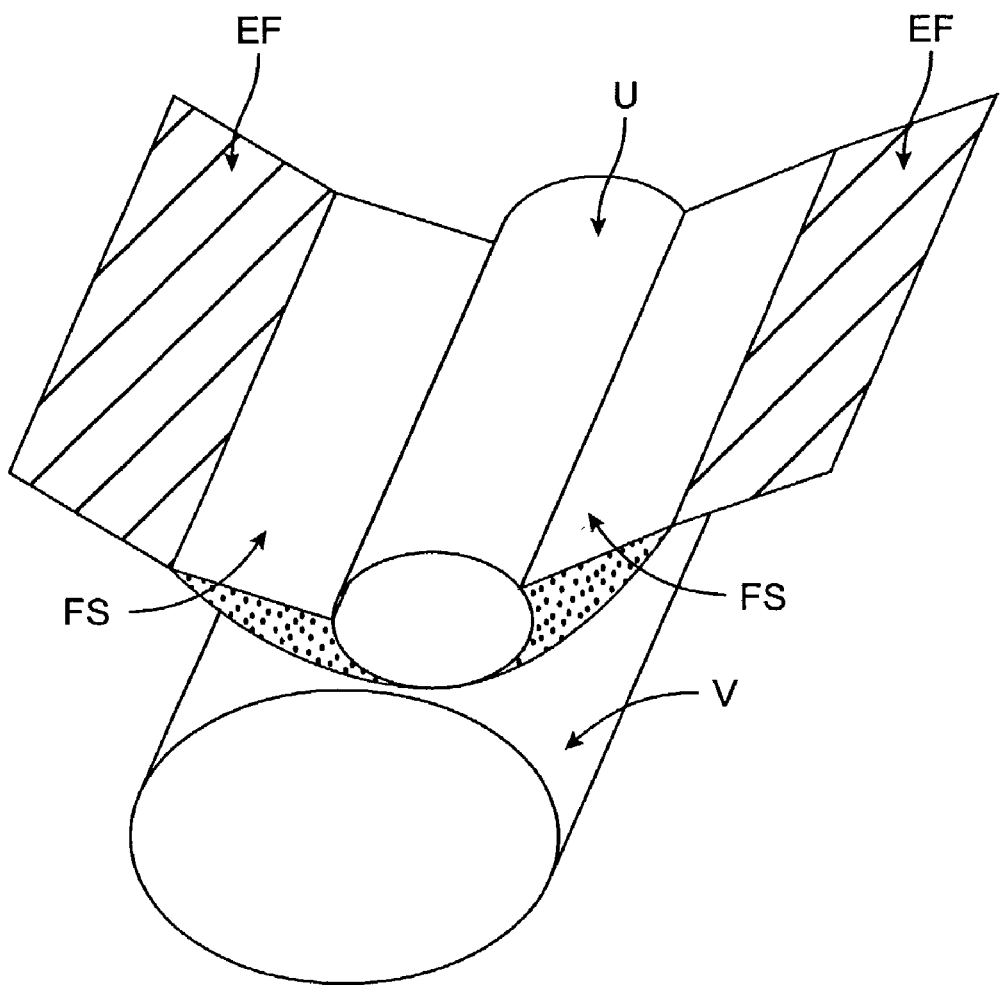
FIG. 8 is a simplified cross sectional front view of target tissue of an exemplary method of the present invention.

In some embodiments of the methods of the present invention, probe body 12 will be configured to be insertable in a second body orifice, while guide shaft 22 will be configured to be inserted into a first body orifice so as to accurately position the probe body 12 and electrodes 18 adjacent a target tissue in the second body orifice. Preferably, the probe body 12 will be positioned in an offset position relative to the guide 22. In a particular method, the guide shaft 22 is configured for insertion into a patient's urethra U while the probe body 12 will be configured for insertion into a patient's vagina V (FIGS. 8 and 9). In such embodiments, urethral guide 22 will generally have a diameter and length that allows a distal end 34 of the urethral guide 22 to extend through the patient's urethra U and into the patient's bladder B. As such, the urethral guide will have a length between approximately 3 inches and 6 inches and a diameter between approximately 0.12 inches and 0.38 inches.

As illustrated in FIGS. 8 and 9, the urethra U is supported by triangular shaped fascia sheets FS that have nerve bundles. Delivery of electrical energy into the fascia sheets FS is undesirable. The electrical energy is preferably delivered to the endopelvic fascia EF that is spaced laterally to both sides of the urethra. To offset the probe 12 away from the fascia sheets and urethra, a longitudinal axis of guide 22 can be aligned in an angled arrangement with a longitudinal axis of the probe body 12. The angled offset moves the probe body laterally (left or right) away from the urethral tissue and fascia sheets and adjacent the target endopelvic fascia EF for treatment. Because of the offset configuration between guide 22 and probe 12, the electrodes 18 will be offset from urethra U and moved against the target tissue that is laterally spaced from the urethra (FIG. 8). In order to provide accurate positioning, in some embodiments, urethral guide 22 is substantially rigid so as to maintain its relative position between the electrode 18 and guide shaft 22. As such, guide 22 is also typically in the form of a rigid shaft. In some embodiments, rigid guide 22 is at least partially composed of or covered with a bio-compatible material that is typical of intraurethral catheter devices. If the guide shaft is too flexible, then the position of the electrodes 18 relative to the guide shaft 22 may not be maintained in the desired position and electrical energy may be inadvertently delivered to non-targeted tissue (e.g. urethra and nerve bundles surrounding urethra).

Figure 10:
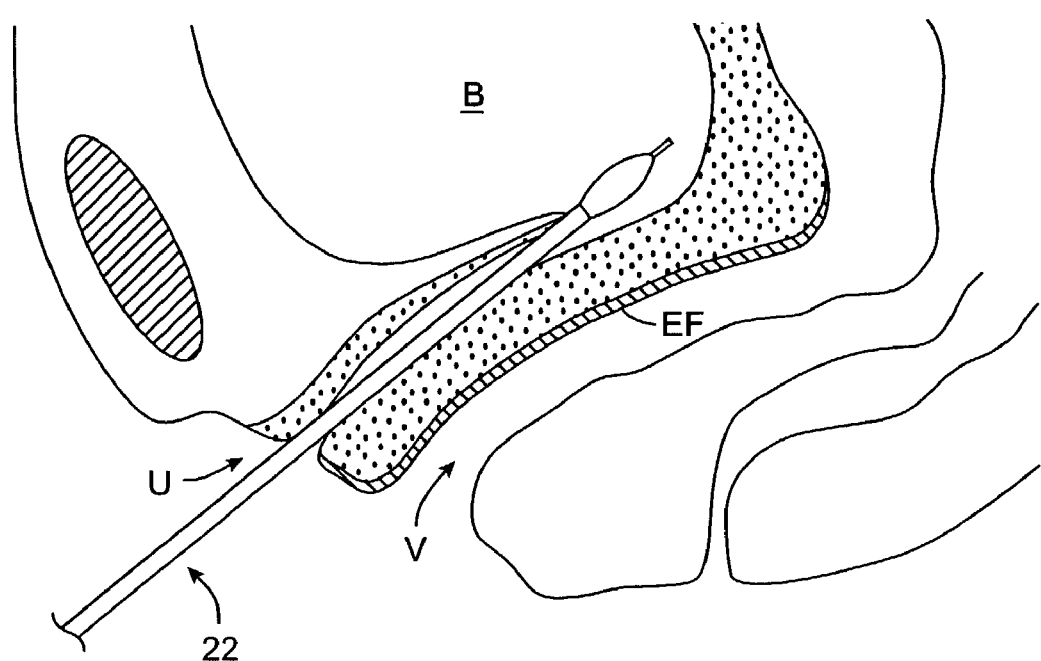
FIG. 10 illustrates placement of an embodiment of the guide into the urethra.
Figure 11:
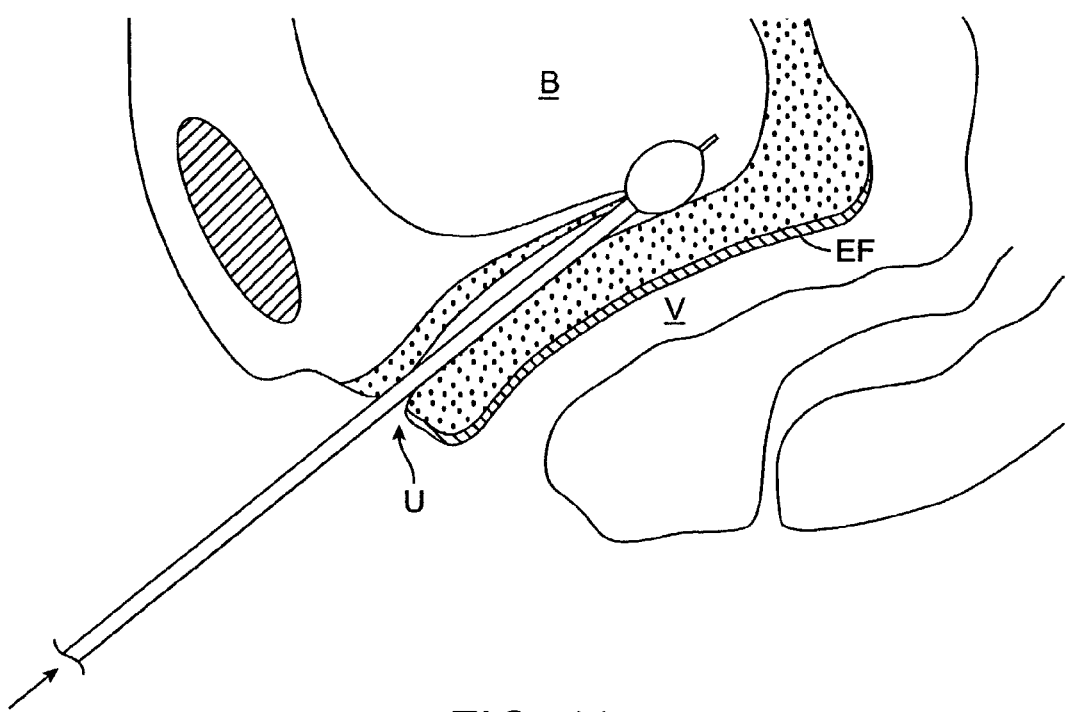
FIG. 11 illustrates expanding of the expansible member in the bladder.

An exemplary embodiment of a method of the present invention is illustrated in FIGS. 10–13. In a noninvasive medical procedure to treat incontinence, the urethral guide 22 can be inserted into the urethra U (FIG. 10). During its distal movement through the urethra U, expansible member 42 will be in its deflated configuration. Once the expansible member enters the orifice to the bladder B, expansible member 42 can be inflated to "lock" the position of the urethral guide 22 to prevent proximal retraction of the urethral guide 22 out of the bladder B (FIG. 11). In some embodiments, the urethral guide can include markings to ensure that the urethral guide remains in the most proximal position allowed by the expansible member relative to the bladder neck orifice. If desired, any liquid that is present in the bladder B can be drained out of the bladder B through the distal orifice 48 and fluid channel 46 within the urethral guide.

Figure 12:
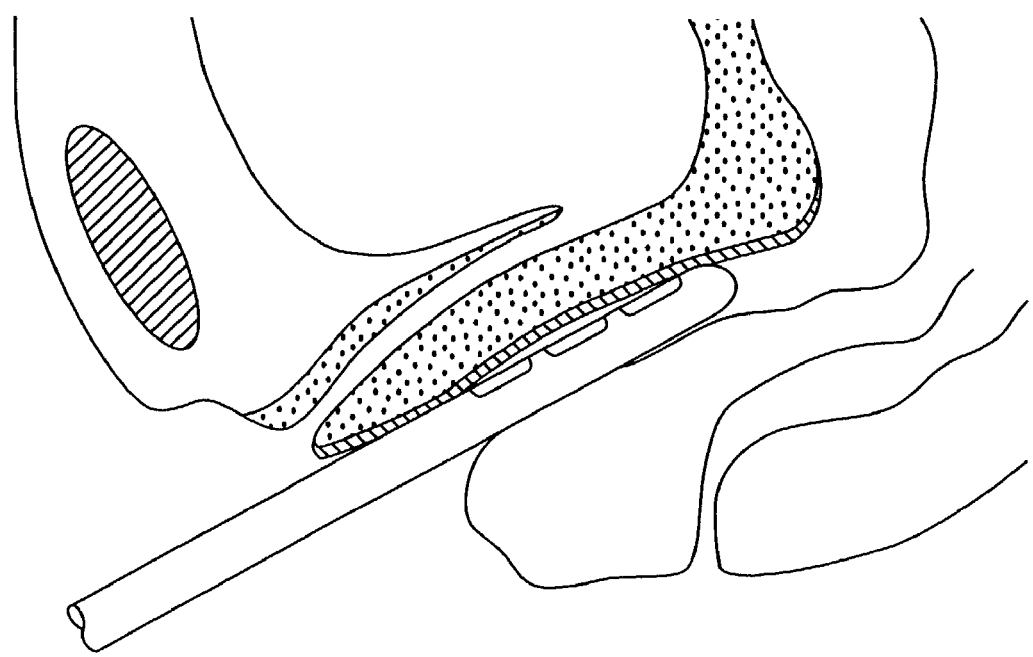
FIG. 12 illustrates placement of the probe into the vagina.
Figure 13:
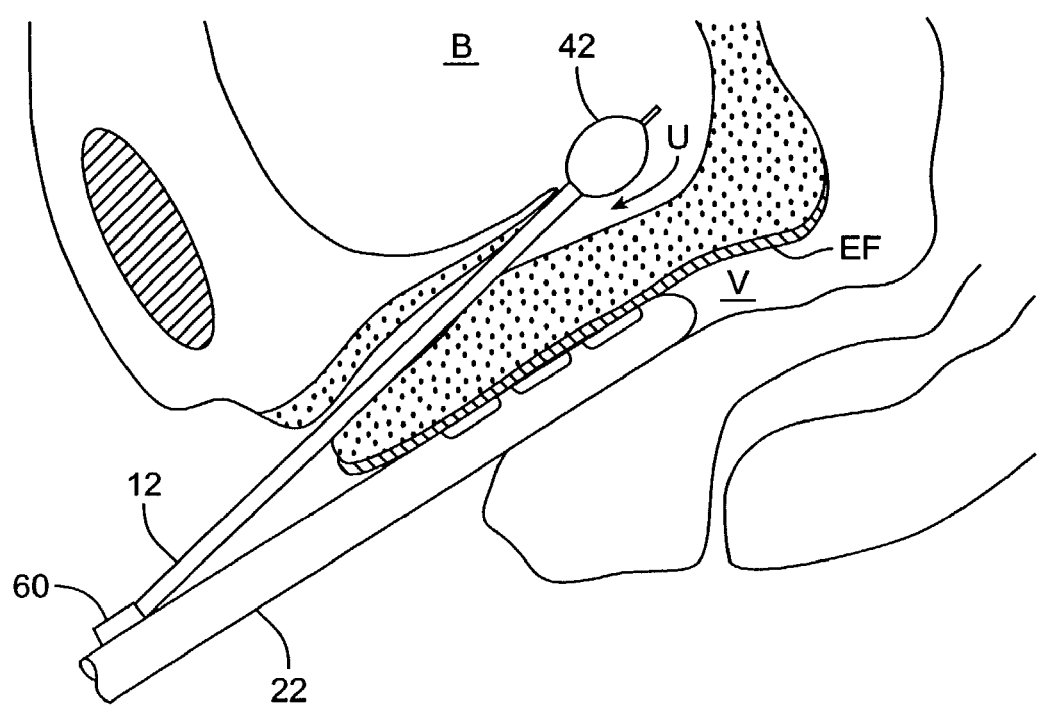
FIG. 13 illustrates coupling of the guide to the probe body in an offset configuration and treating the target tissue.

FIG. 12 illustrates that the probe body 12 can be inserted into the patient's vagina V (for clarity guide 22 is not shown). Once it is grossly determined that the probe has been inserted to the proper location the urethral guide and probe body can be attached together with the coupling structure 60 (FIG. 13). Such coupling will ensure that the distal tip of the probe body 12 is maintained proximal of the distal end of the guide 22 so as to position the treatment surface adjacent the target endopelvic fascia EF and to prevent the electrodes from delivering electrical energy to the bladder or other non-target tissue. The coupling structure also will maintain the offset configuration between the axes of the guide 22 and probe body 12 so as to position the electrodes offset laterally away from the urethra and towards the target tissue EF. Optionally, if the guide 22 is positioned below a top plane of the electrode, the guide may tension the tissue and bias the electrodes 18 into the target tissue EF.

While FIGS. 10 and 12 illustrate the urethral guide 22 and probe body 12 being separately inserted into the body orifices, it should be appreciated that in alternative embodiments, the urethral guide 22 and probe body 12 can be simultaneously inserted into the urethra U and vagina V while fixedly or rotatably connected with coupling structure 60, 86.

Some alternative methods of registering the urethral guide and probe will now be described. FIGS. 14 to 18B illustrate other embodiments of probe 12 and urethral guide 22 of the present invention that incorporate a passive registration assembly to position probe 12 in a position relative to urethral guide 22 so as to position the treatment surface 18 adjacent the target tissue. In the illustrated embodiments, urethral guide 22 is configured to be maintained in a detached position relative to probe 12. Urethral guide 22 and probe 12 can include landmarks such as an expansion member, palpation member, or other sensors or transmitter markers that indicate a mid urethra point. The marker(s) can be placed in the vagina or the marker can be placed in the urethra and sensed through the vaginal wall.

Figure 14:
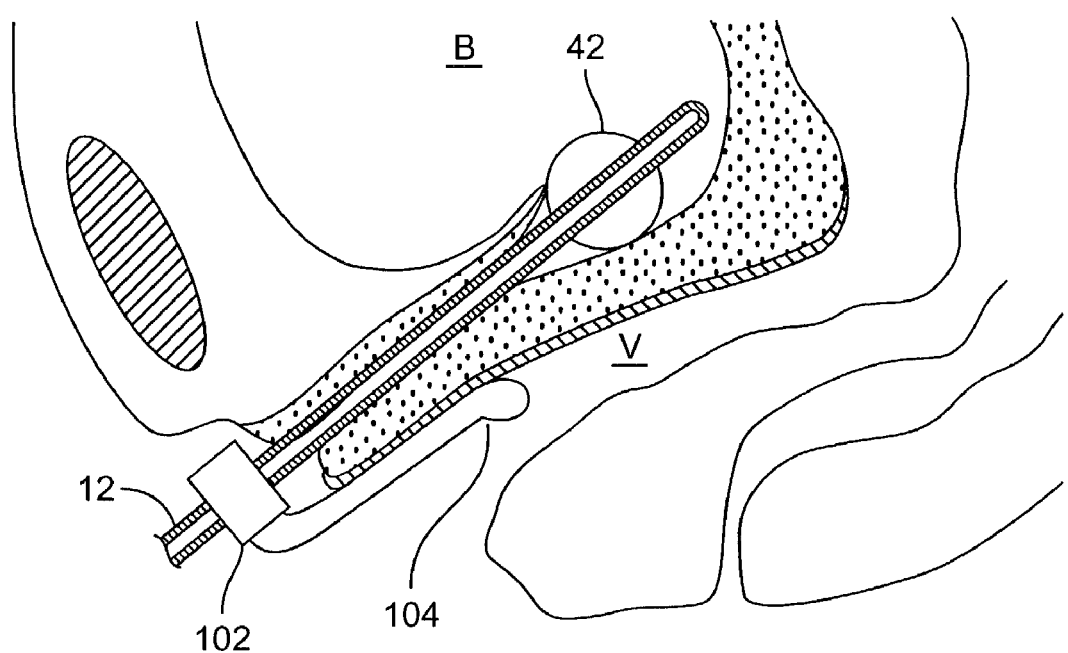
FIG. 14 illustrates an embodiment that includes a mechanical palpation member coupled to the urethral guide to indicate a mid-urethra point.
Figure 15:
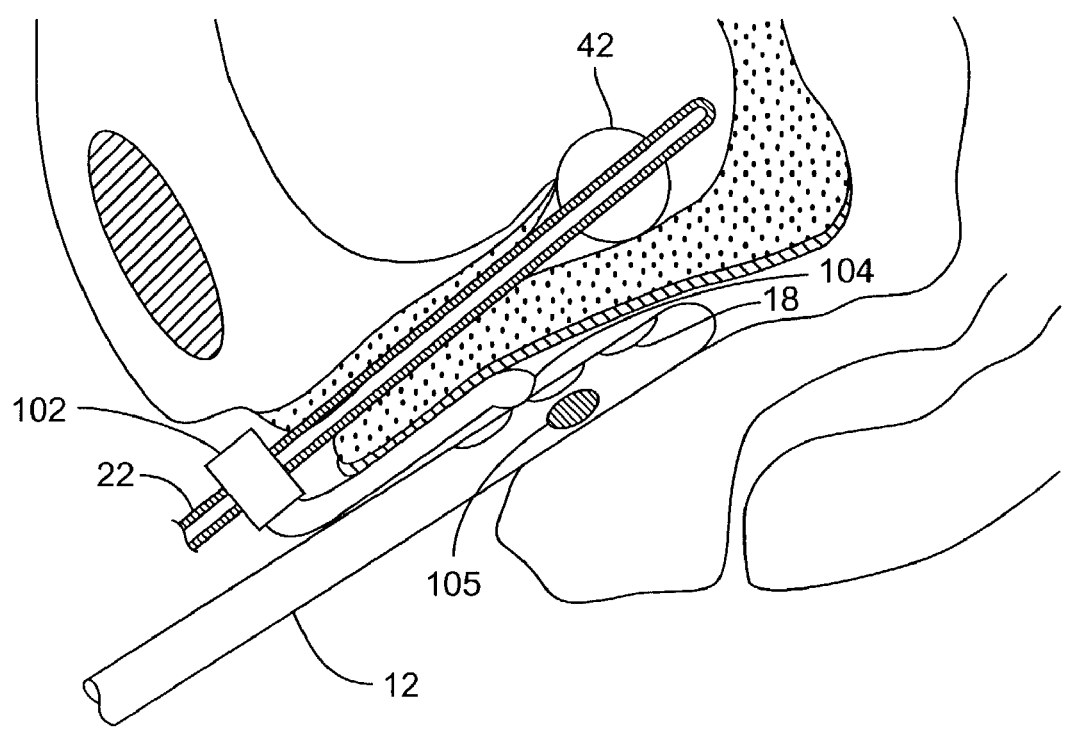
FIG. 15 illustrates the urethral guide of FIG. 14 with a probe.

In the embodiment illustrated in FIGS. 14 and 15, a physical marker can be used to help position probe 12 relative to urethral guide 22. While probe 12 and urethral guide 22 are not physically connected, the relative position and/or spacing of the probe 12 and urethral guide 22 can be used to indicate to the physician as to whether or not the treatment surface 18 of probe 12 is positioned adjacent the target tissue.

After urethral guide 22 is positioned in the urethra U, a bobby-pin type clip or a U-clip 102 can be coupled to the urethra guide to provide a physical marker in the vagina for the physician. In one embodiment, U-clip 102 can include a palpation member 104 at a distal end that will be positioned in the vagina to allow the physician to feel the mid-urethra point. In such embodiments, probe 12 can also include a corresponding palpation members 105, such that when the probe is inserted into the vagina, the physician can proximally/distally align and laterally offset palpation markers 104, 105 so as to position the treatment surface adjacent the target tissue and offset from the non-target urethral tissue.

Palpation members 105 can be opposed bumps or indentations, an enlarged portion of probe body, an embossed marking, or any other element that allows the physician to determine by physical contact, a position of the treatment surface 18. In one embodiment, palpation members 105 will be on opposite sides of the probe body and separate from the treatment surface 18. In other embodiments, however, the palpation members 105 can be positioned on other surfaces of the probe body, such as on the treatment surface 18 or the like.

Figure 16:
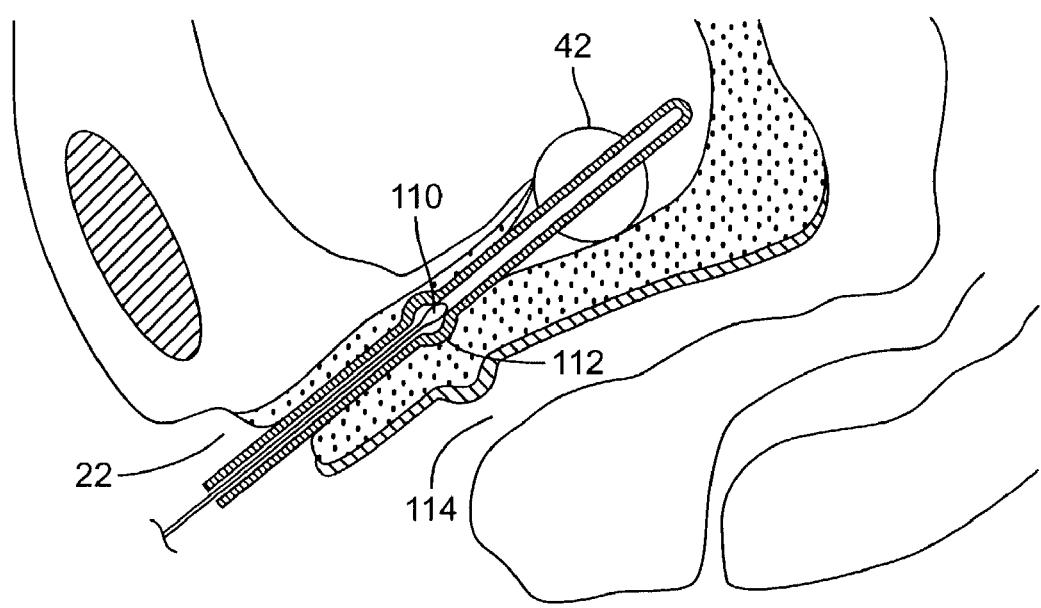
FIG. 16 illustrates yet another embodiment of an urethral guide of the present invention that includes an expansion member.
Figure 17:
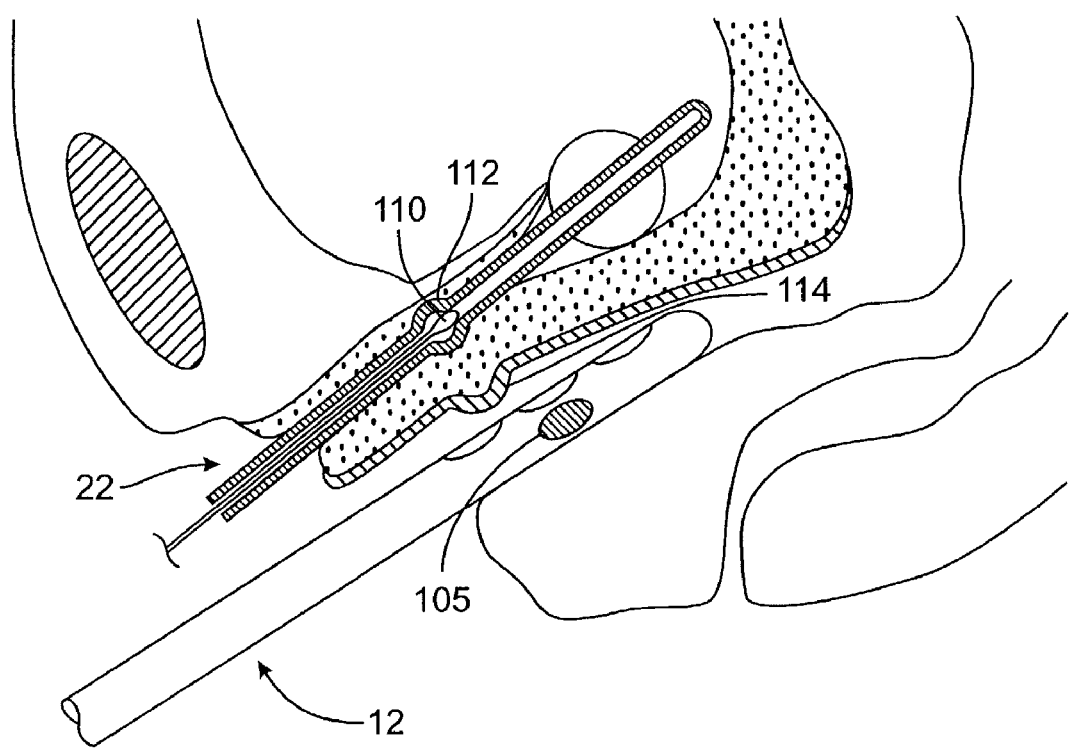
FIG. 17 illustrates the urethral guide of FIG. 16 and a probe of the present invention.

In the embodiments illustrated in FIGS. 16–18B, instead of providing a marker in the vagina, the urethral guide 22 can be configured to provide a marker of the mid-urethra point through the vaginal wall. For example, as shown in FIG. 16, urethral guide 22 can include an expansion member 110 that creates an expanded region 112 in urethral guide 22. Expanded region 112 will be sized so as to create a discernible bulge or bump 114 in a vaginal wall. The physician can then manually feel along the upper vaginal wall to find bulge 114 and use bulge 114 as a marker for the palpation members 105 on probe 12. Similar to above, as shown in FIG. 17, the physician can then position the treatment surface in a laterally offset and proximally/distally aligned position relative to bulge 114 by aligning palpation members 105 with bulge 114 and positioning the treatment surface adjacent the target tissue in the vagina.

In one embodiment, palpation members 105 can be positioned laterally from the bump 114 or palpation member 104 between approximately 1 cm and 2 cm and should not be positioned proximal or distal of the bump. As can be appreciated, however, it may not always be possible to proximally/distally align the palpation members 120 with bump 104, and a proximal or distal offset of between approximately ±5 mm may be acceptable for delivering a treatment to the target tissue.

FIG. 18A illustrate one embodiment of a simplified urethral guide in a relaxed position and FIG. 18B illustrates the urethral guide in an expanded position. Urethral guide 22 includes an expansion member 110 and an outer tubular member 130 that defines at least one inner lumen 132. A second tubular member 133 can be disposed within lumen 132 such that an expandable region 112 will be positioned near a center point of urethral guide 22. Positioning can be achieved by first measuring the urethral length with a marked urethral guide and pullback of the distal balloon 42 to the bladder neck. Marks on the inner lumen of the urethral guide permit its insertion to the correct distance based on the then known patients urethral length. An elongate shaft 136 can include the expansion member 110, such as a wedge, balloon, or the like, at or near its distal end. Elongate shaft 136 can be movably disposed within lumen 132 such that proximal actuation of elongate shaft 136 by the physician moves expansion member 110 into expandable region 112 so as to enlarge the diameter of outer tubular member 130 from a first width 140, to a second, larger width 142 (FIG. 18B). The expansion of the outer tubular member 130 can be used to create bulge 114 in the vaginal wall.

FIGS. 19A to 20B illustrate other embodiments of urethral guide 22 and probe body 12 which utilize an automatic electromagnetic coupling to assist the physician in positioning the probe body 12 adjacent the target tissue. In the embodiment illustrated in FIG. 19A, an RF coupling can be used to transmit and receive RF energy waves 151 to monitor the position of the probe relative to the urethral guide. One or more RF transmitters 150 can be coupled to urethral guide 22 to generate RF energy waves 151. In the illustrated embodiment, a plurality of RF transmitters 150 are positioned around a portion of guide 22 that will be positioned at the mid-urethra. Probe body 12 can include one ore more RF receivers 152. In the illustrated embodiment, probe body 12 can include a plurality of RF receivers that are positioned around the treatment surface. While the RF receivers 152 are illustrated on the treatment surface, it can be appreciated that the RF receivers 152 can be positioned within probe body 12, along a bottom surface of probe body, and/or separate from RF receivers. RF receivers 152 need only be positioned on probe body 12 to indicate the relative position of the treatment surface.

Figure 19A:
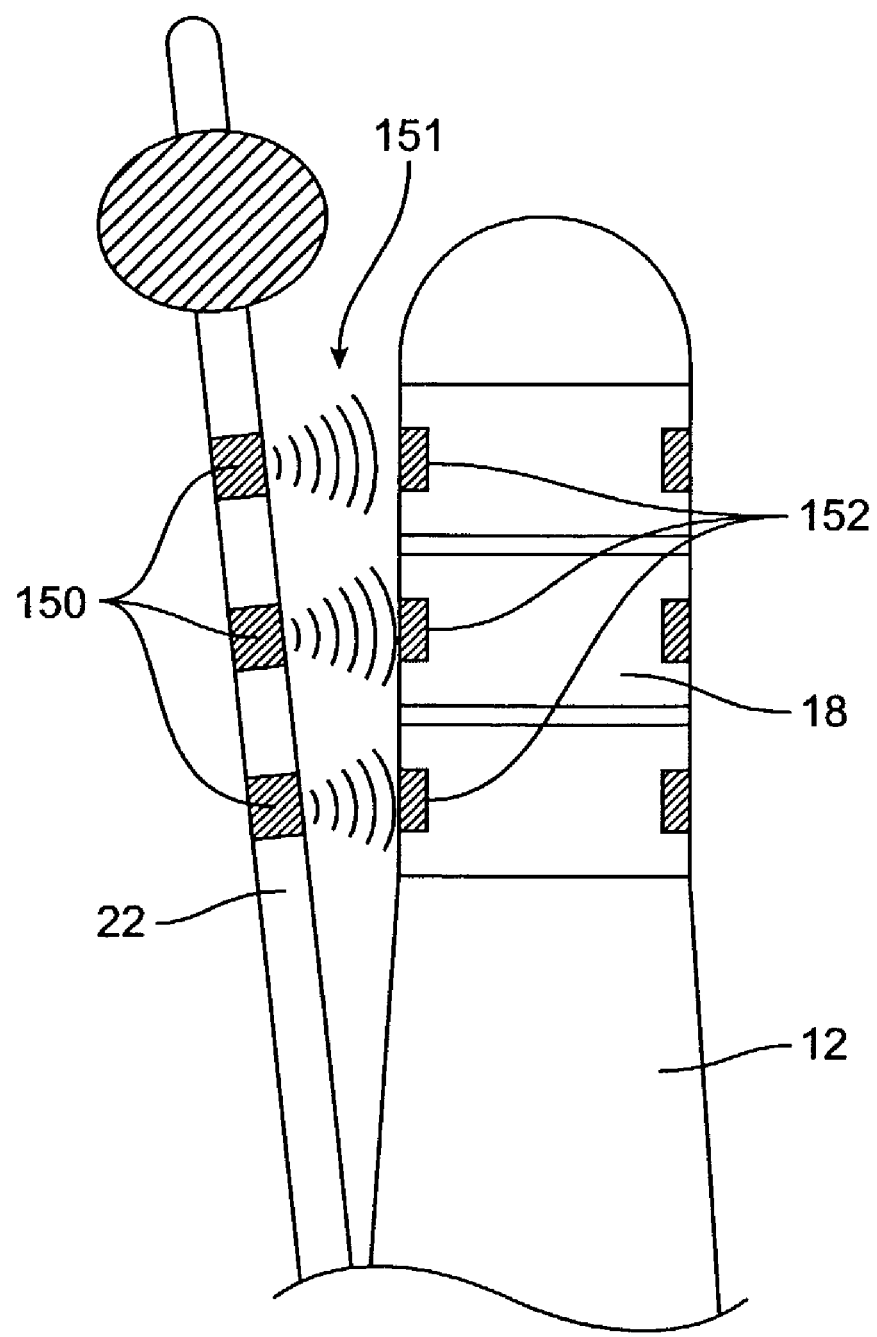
FIGS. 19A and 19B illustrate an embodiment that includes RF coupling.
Figure 19B:
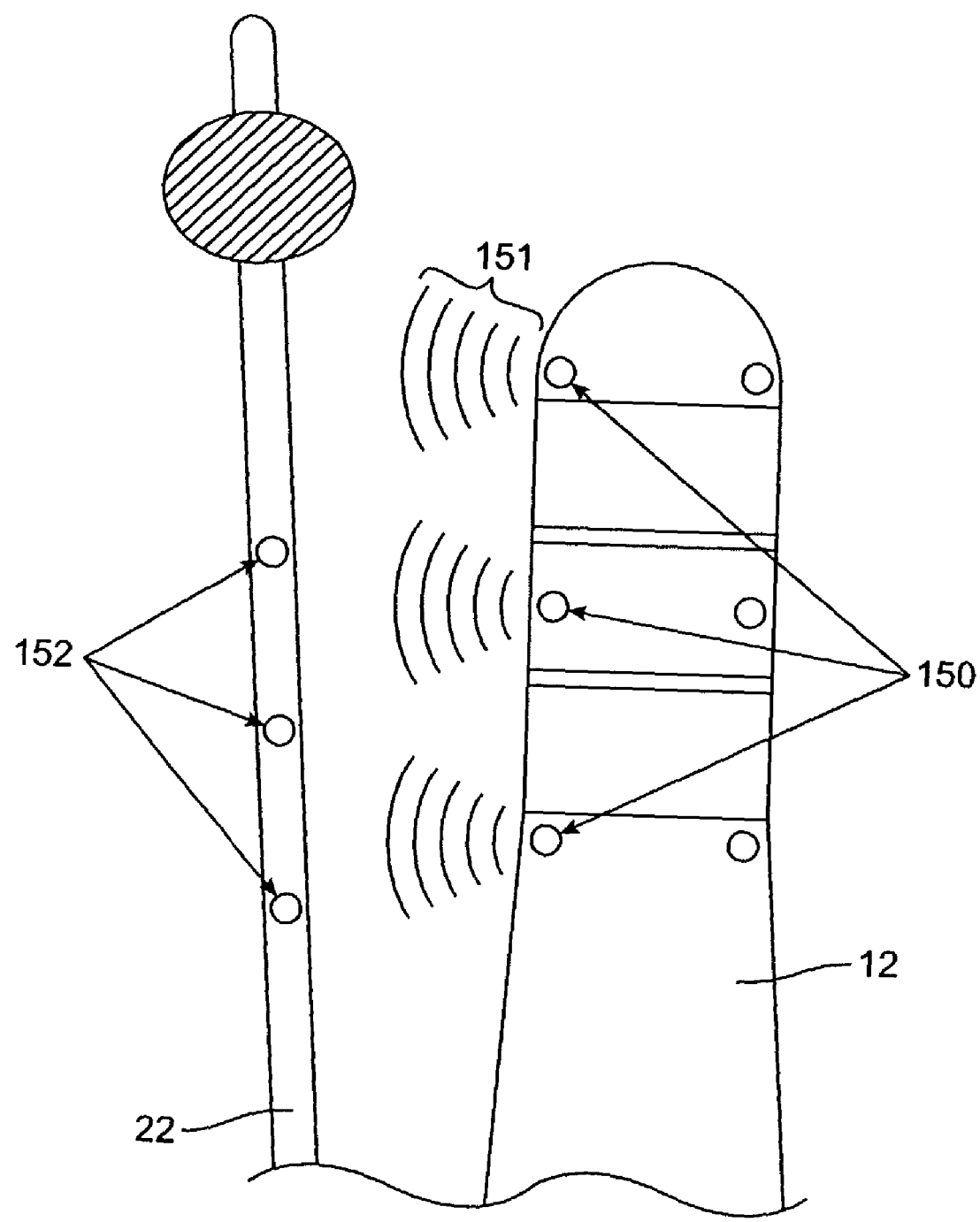

In another embodiment, illustrated in FIG. 19B, the RF transmitters 150 can be positioned on probe body 12 while RF receivers 152 can be positioned on urethral guide 22.

Figure 20A:
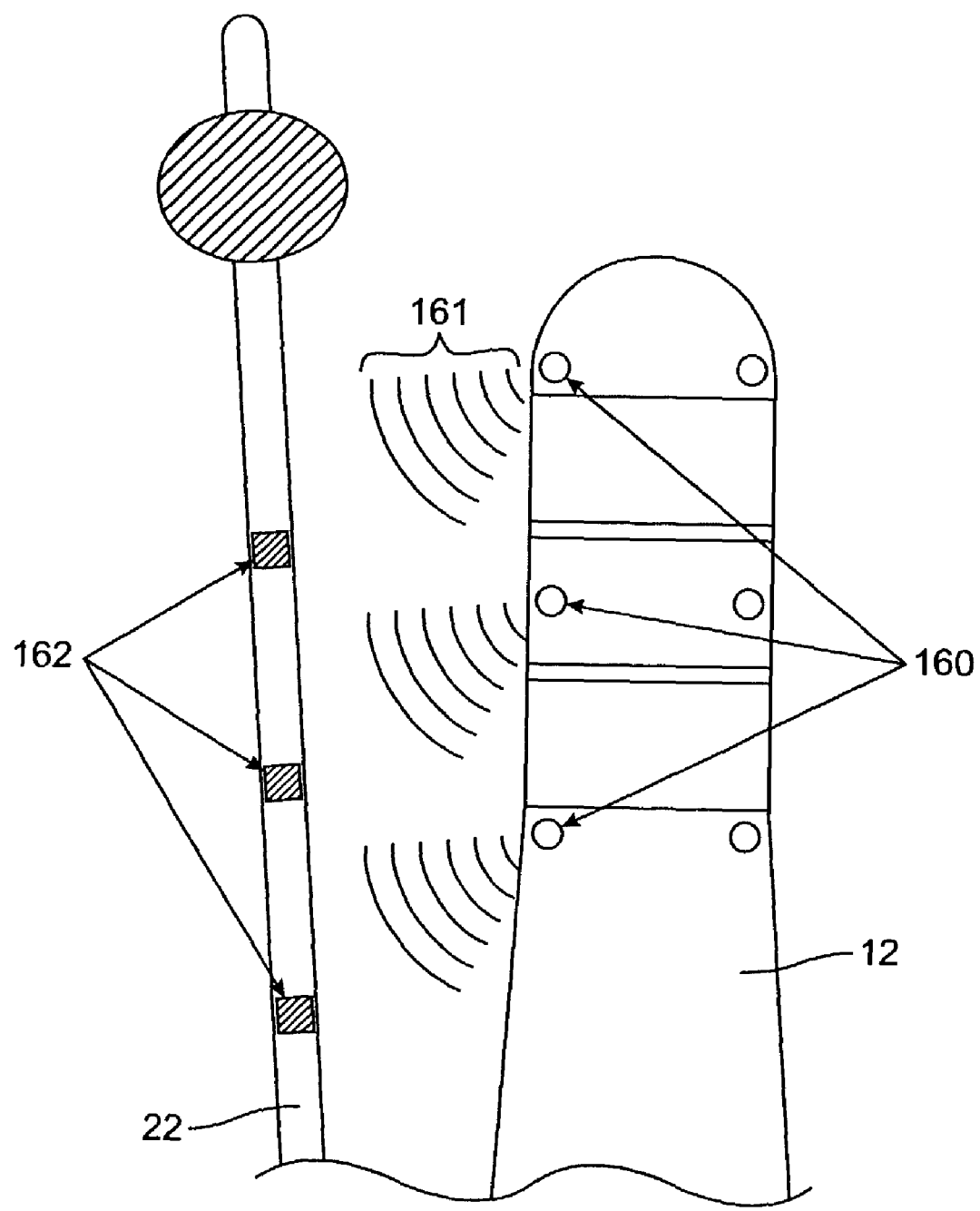
FIGS. 20A and 20B illustrate an embodiment that include a magnetic coupling.
Figure 20B:
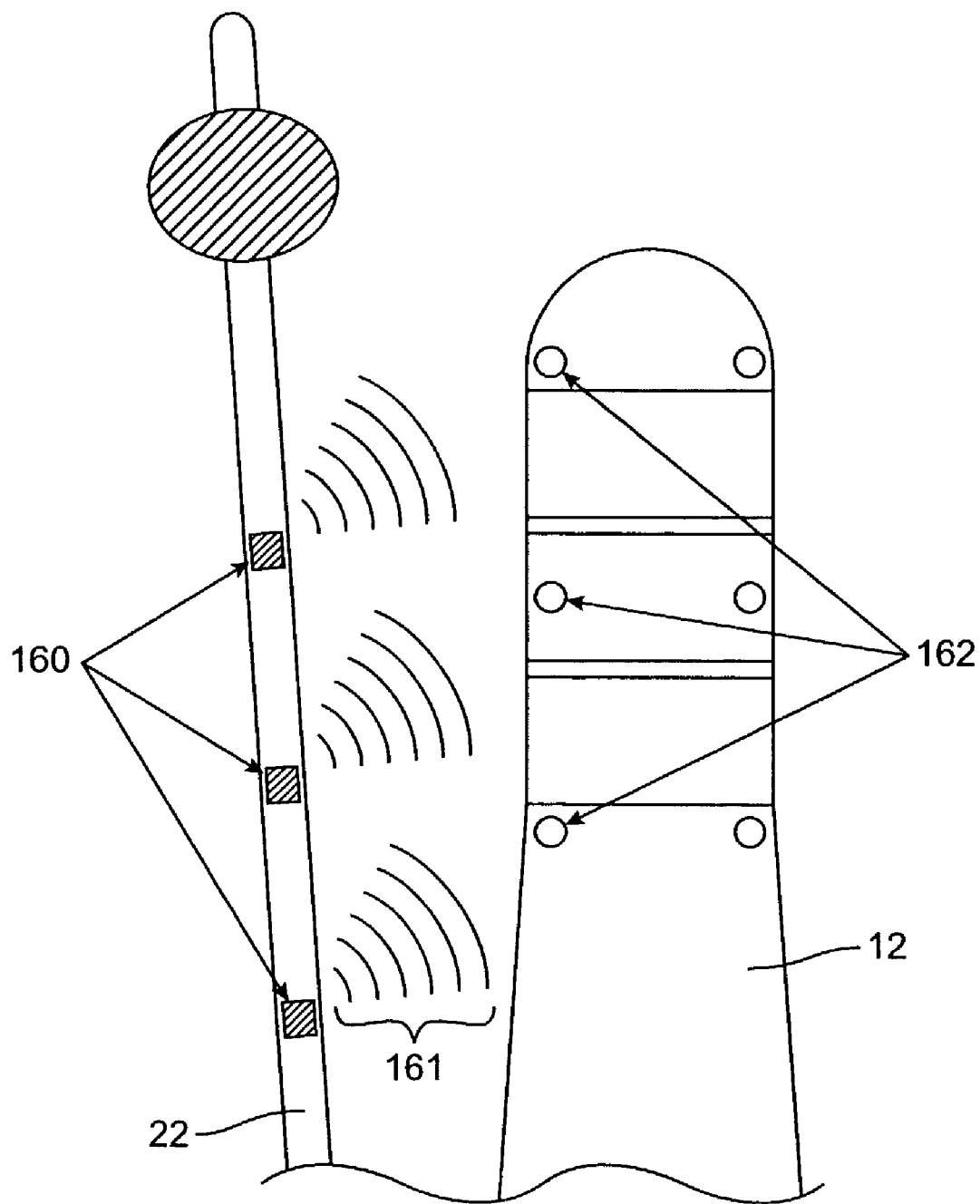

FIGS. 20A and 20B illustrate another embodiment of probe 12 and guide 22 which use an magnetic coupling to register the probe body 12 with guide 22. Similar to above, the embodiment illustrated in FIG. 20A, the urethral guide 22 can include one or more magnetic source(s) 160, such as a magnet to generate a magnetic field 161. Probe body 12 can include one or more magnetic field sensors 162, such as a Hall Effect Sensor to sense the strength of the magnetic field 161 created by the magnetic sources 160. The strength of the magnetic field generated by magnetic source 160 and sensed by the magnetic sensors 162 will produce a signal that is proportional to the spacing between the source 160 and sensors 162. The magnetic field can be sensed by sensors 162 and the signal from the sensors can be transmitted to a controller CPU (not shown) to determine the position of the probe 12 relative to the urethral guide 22.

As illustrated in FIG. 20B, in an alternative embodiment, the magnetic sensors 162 can be positioned on urethral guide 22 and magnetic sources 160 can be positioned on probe body 12.

Figure 21:
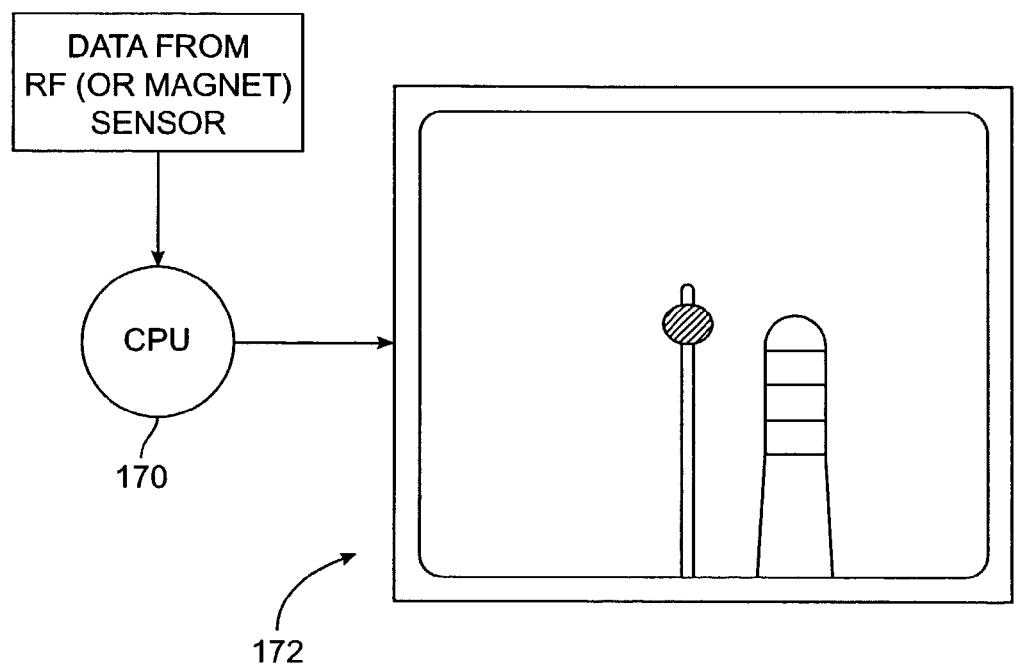
FIG. 21 schematically illustrates a CPU of a controller coupled to an output display that shows a graphic representation of the urethral guide and probe.

In any of the electromagnetic coupling embodiments, the transmitters 150, 160 will emit an position signal that will be received by sensors 152, 162 that will indicate the relative position of the probe body 12 relative to urethral guide 22. As illustrated in FIG. 21, in some embodiments, the data from the sensors can be transmitted to a CPU 170 of controller so as to generate a graphic representation of urethral guide and probe body on an output display 172. CPU 170 can analyze the real-time data received from the sensors to provide direct feedback to the physician regarding the probe body 12 location within the patient's vagina.

Figure 22:
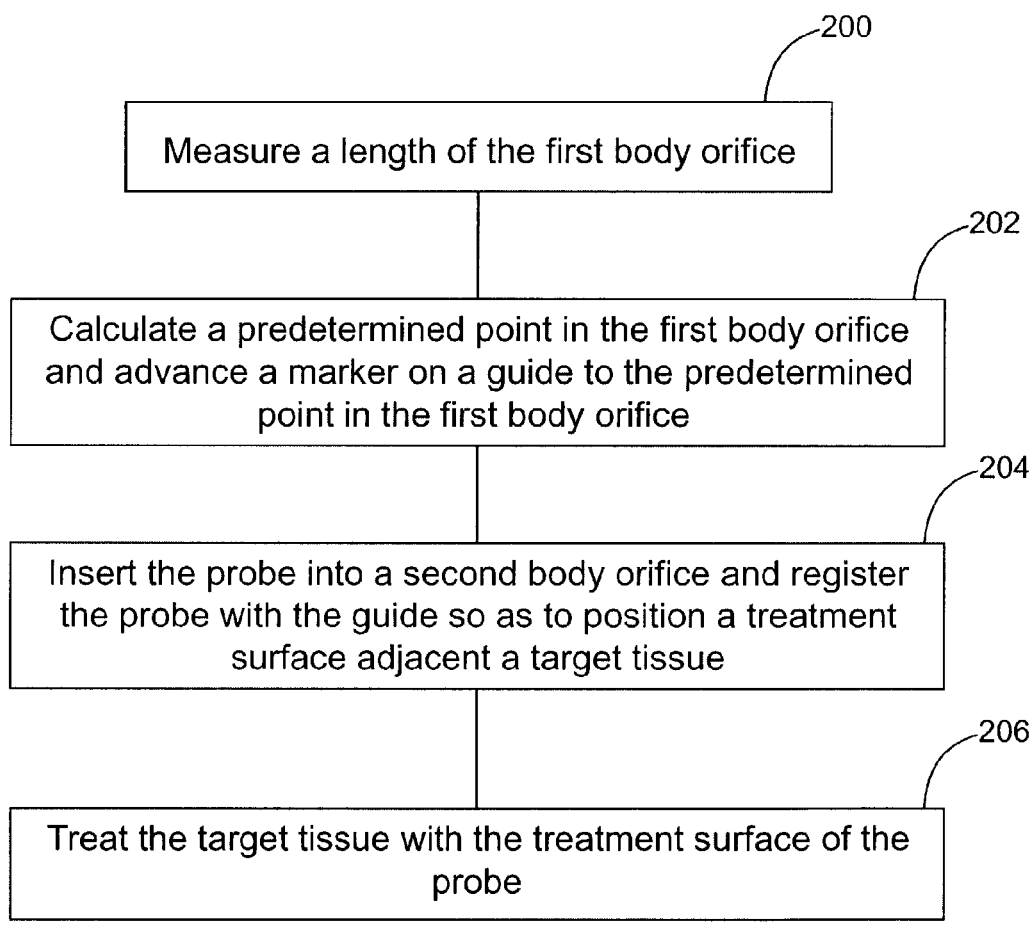
FIG. 22 schematically illustrates a simplified method of the present invention.

Some embodiments of the methods of the present invention will now be described. As illustrated schematically in FIG. 22, some methods of the present invention include the step of measuring a length of the first body orifice (e.g., urethra), 200. In some embodiments such as that shown in FIGS. 24A to 24F, it may be possible to directly place the sensor or palpation device at the mid-urethra position without measuring the length of the first body orifice.

After the length of the first body orifice is determined, a marker (e.g., transmitter, receiver, or physical marker) of the guide can be advanced into the first body orifice and positioned at a predetermined point (e.g., halfway into the length of the urethra or the mid-urethra) which will allow for proper positioning of the probe, 202. After the guide has been properly positioned, the probe can be inserted into the second orifice and registered with the guide, 204. After the probe has been placed in a predetermined position relative to the guide, the target tissue can be treated with a treatment surface of the probe, 206.

A variety of conventional and proprietary methods can be used to measure the length of the first body orifice and to calculate the predetermined distance. For example, in the embodiments in which the first body orifice is the urethra, the physician may manually measure the length of the urethra and then calculate the mid-urethra point (approximately half the length of the urethra).

One embodiment of a device and method for measuring the length of the urethra and locating its midpoint is illustrated in FIGS. 23A to 23F. The device comprises a sensor rod 210 that includes one or more sensors 212 at or near its distal end 214. Sensor rod 210 can fit within an inner lumen of guide shaft 22. Sensor wires can run through a lumen of the sensor rod to communicate with the controller. Sensor rod 210 can include positioning graduations 216 that assist the physician in positioning the sensor(s) at the midurethra.

Figure 23A:
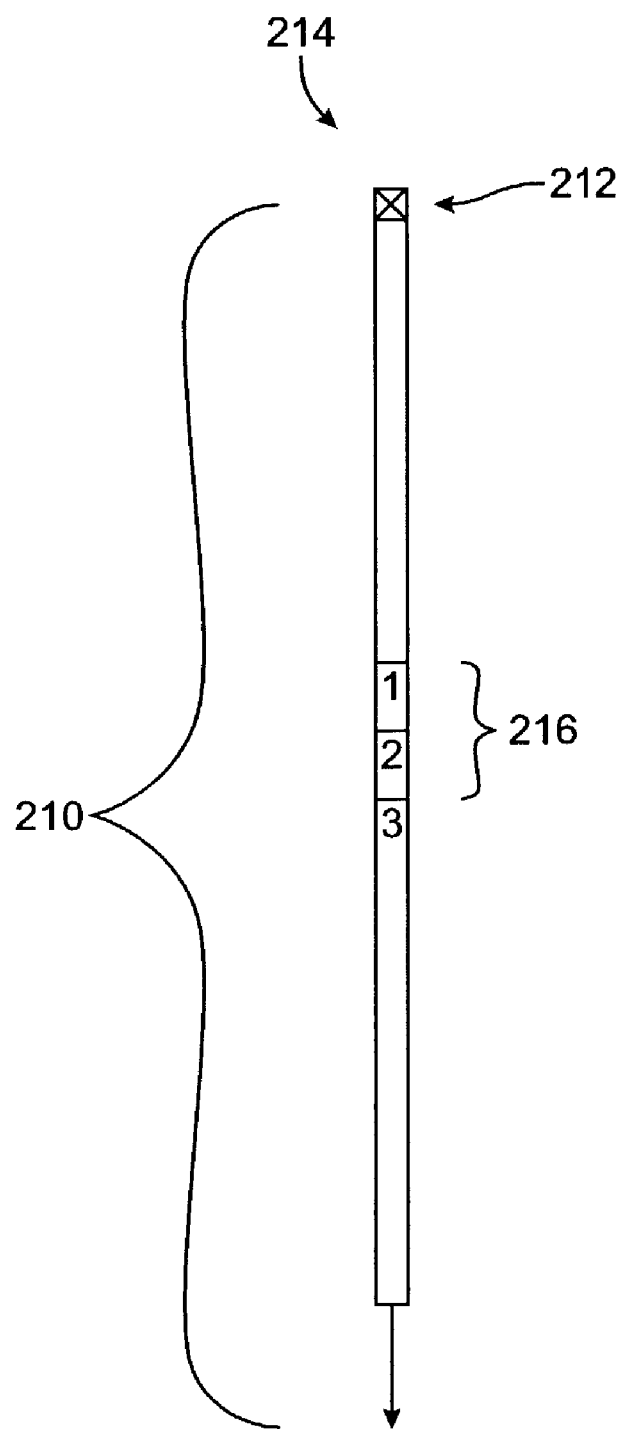
FIG. 23A to 23F illustrate one embodiment of a method and device for measuring a length and a mid-urethral length.
Figure 23B:
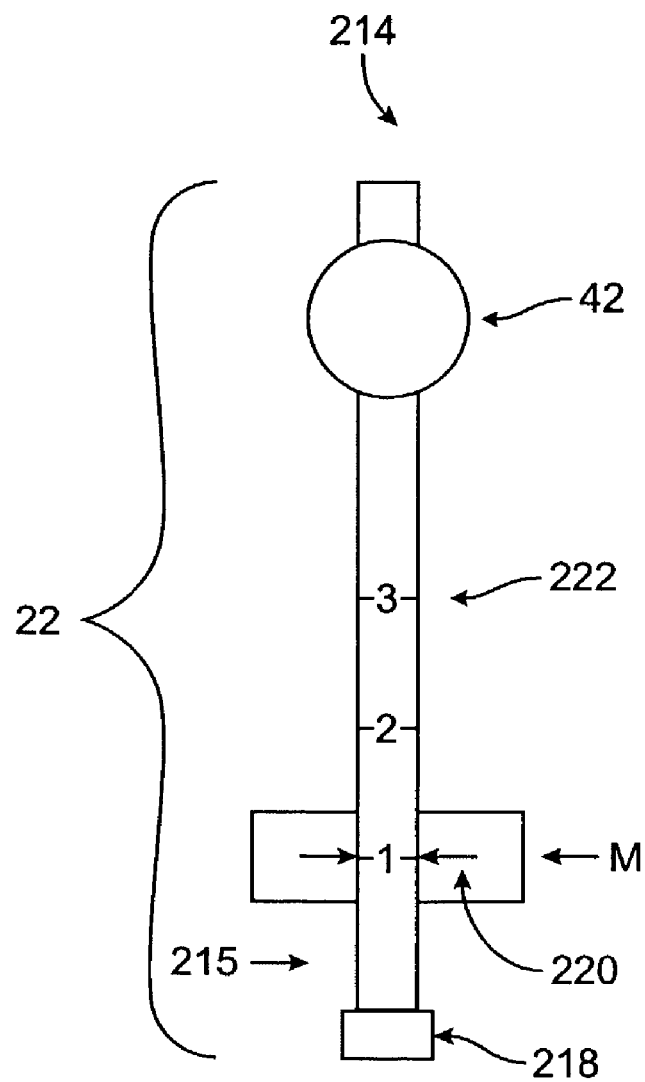

As shown in FIG. 23B, urethral guide 22 can include a balloon 42, a locking mechanism 218 around its proximal end 215 and a sliding stop 220 that can fit over urethral guide 22. Sliding stop 220 can include a marker M, such as an arrow that is configured to align with graduations 222 on the outer surface of the urethral guide to indicate the urethral length.

Figure 23C:
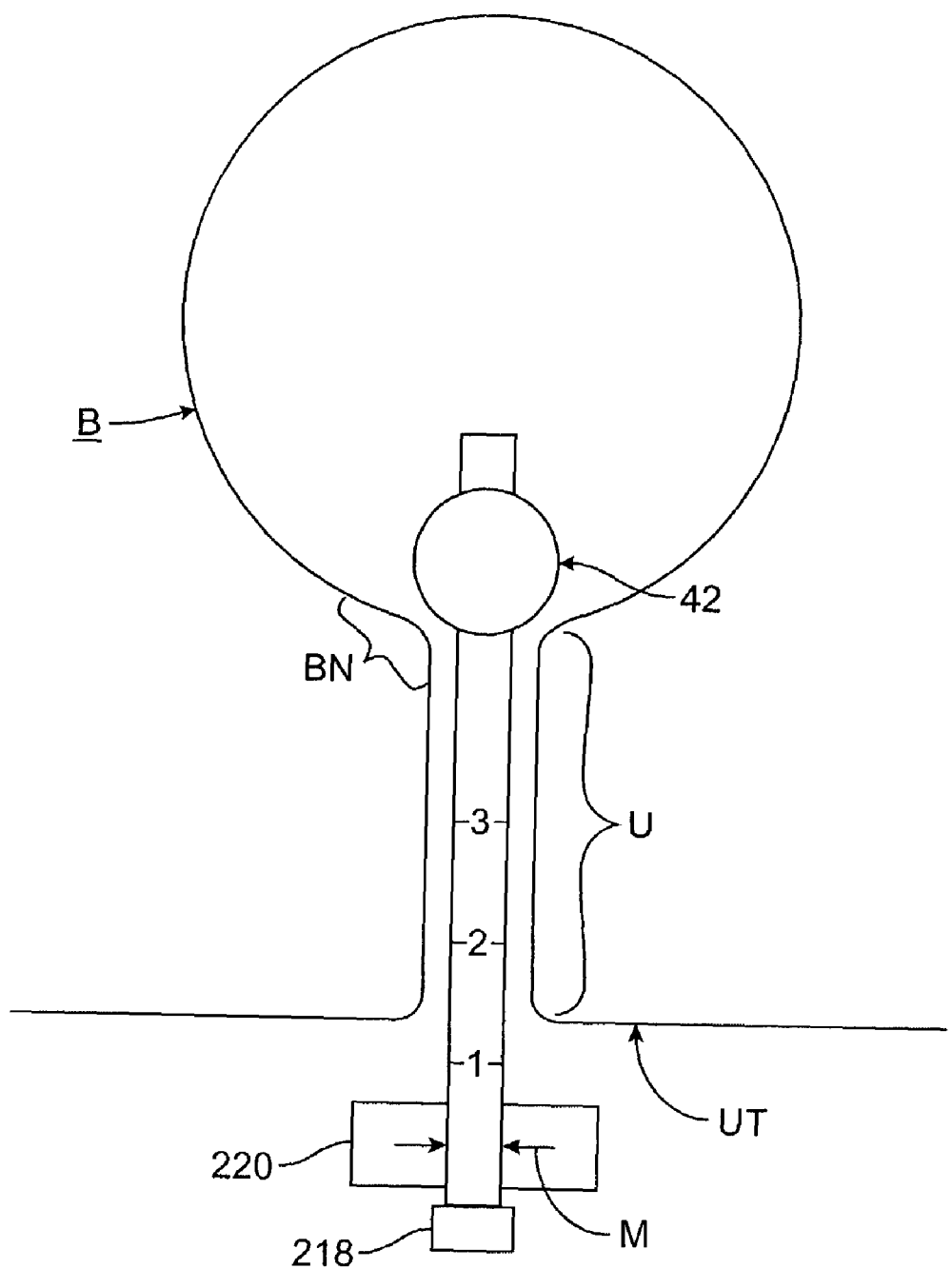
Figure 23D:
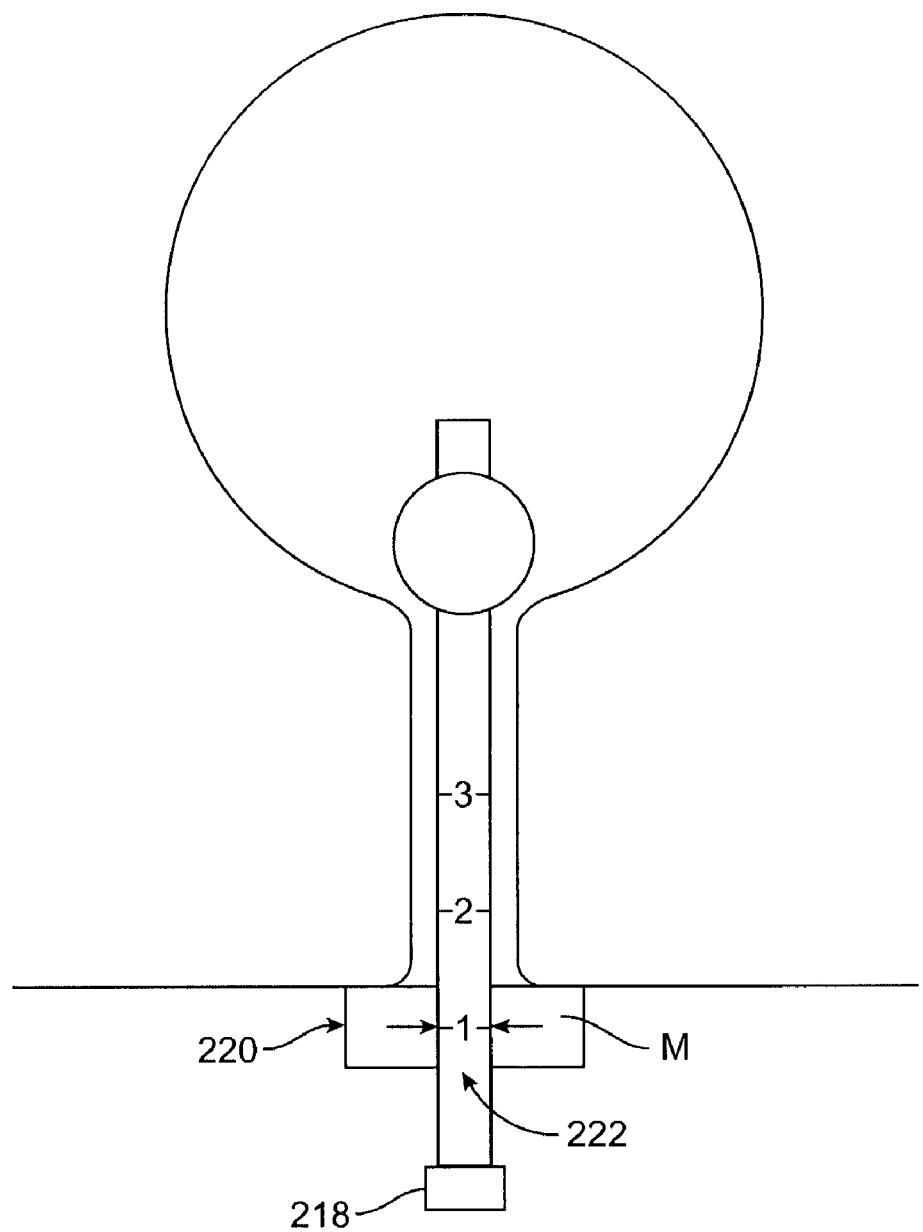

After the urethral guide is inserted into the urethra U and locked into the bladder B with balloon 42, the urethral guide can be pulled proximally to seat balloon 42 against the bladder neck BN. Thereafter, the sliding stop 220 can be pushed distally until it contacts the outer surface of the urethra tissue UT or urethra meatus (FIG. 23C). As shown in FIG. 23D, once the sliding stop has reached the urethral tissue, the sliding stop can be locked into place using spring force on a squeeze clip, expansion pins or a thumbscrew or other similar mechanisms known to those skilled in the art. and the graduation 222 that is aligned with marker M can be read.

Figure 23E:
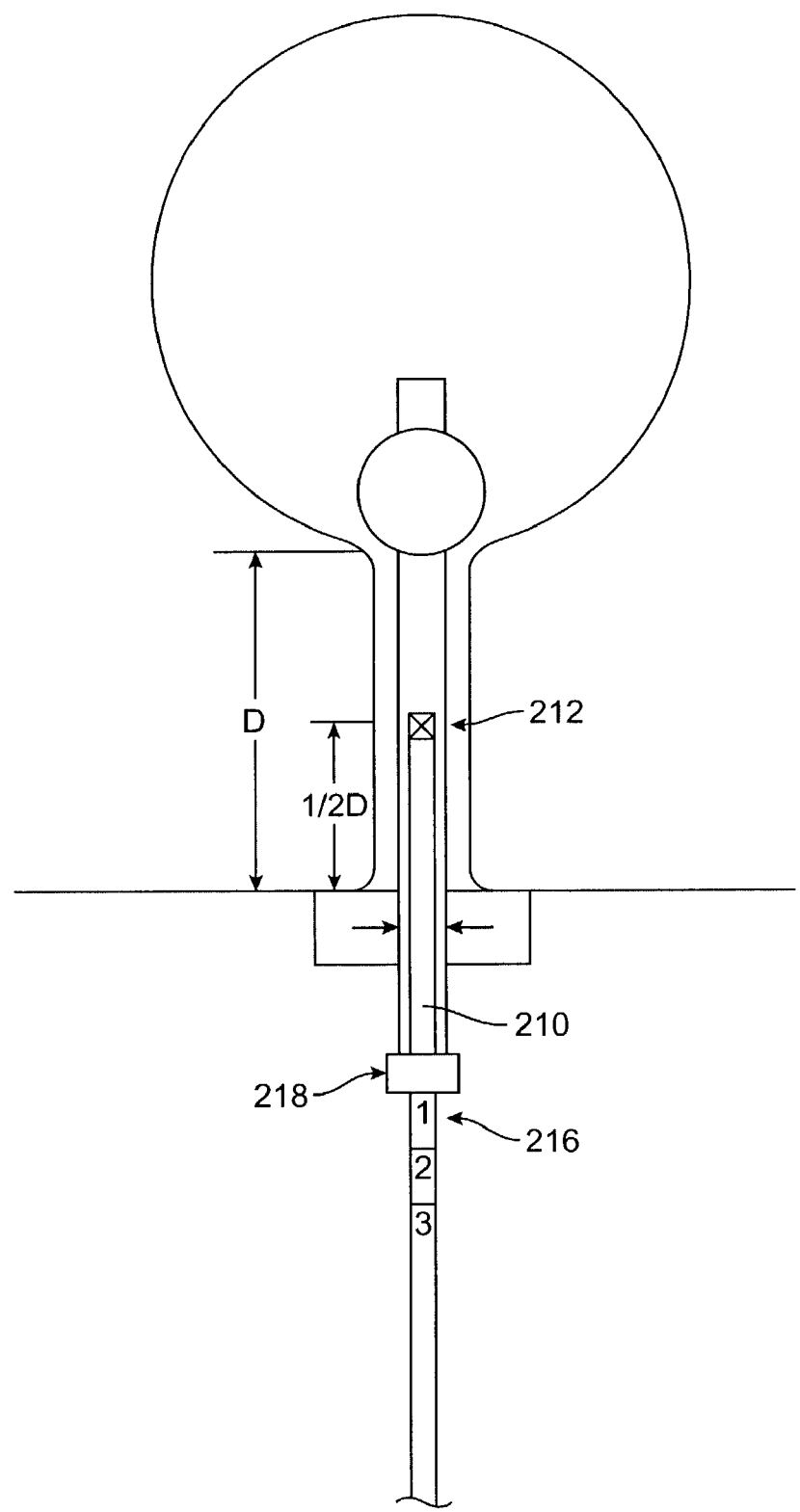
Figure 23F:
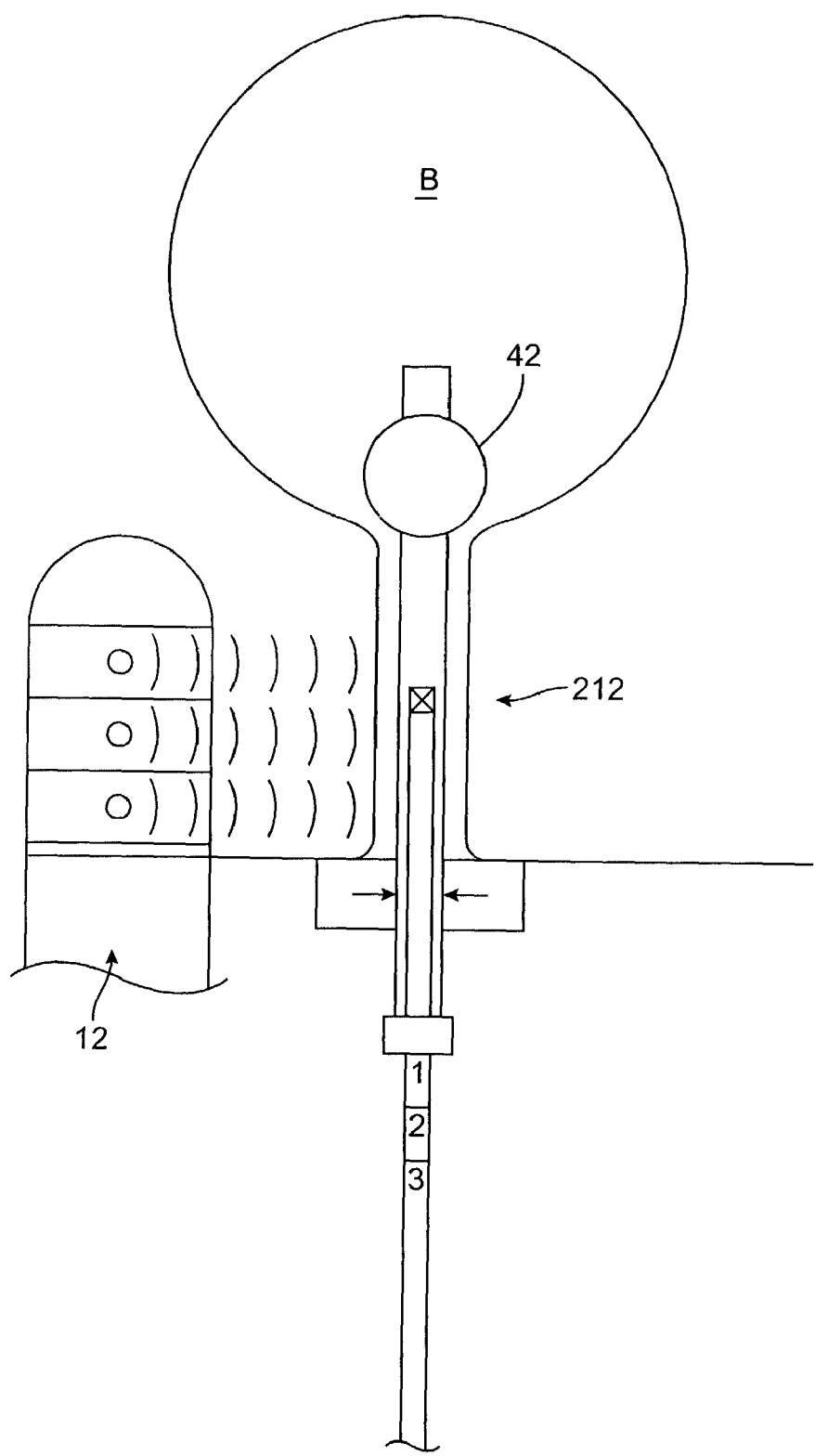

As shown in FIG. 23E, the sensor rod 210 can then be inserted into the inner lumen of the urethral shaft until the graduation 216 that matches the graduation 222 on the guide that is aligned with marker M is aligned with locking mechanism 218. In such a position, sensors 212 will be positioned at approximately the midpoint of the measured length of the urethra. The sensor 212 (or transmitter) can be used to measure or generate a position signal to indicate the position of the mid urethra, as described above (FIG. 23F).

Figure 24A:
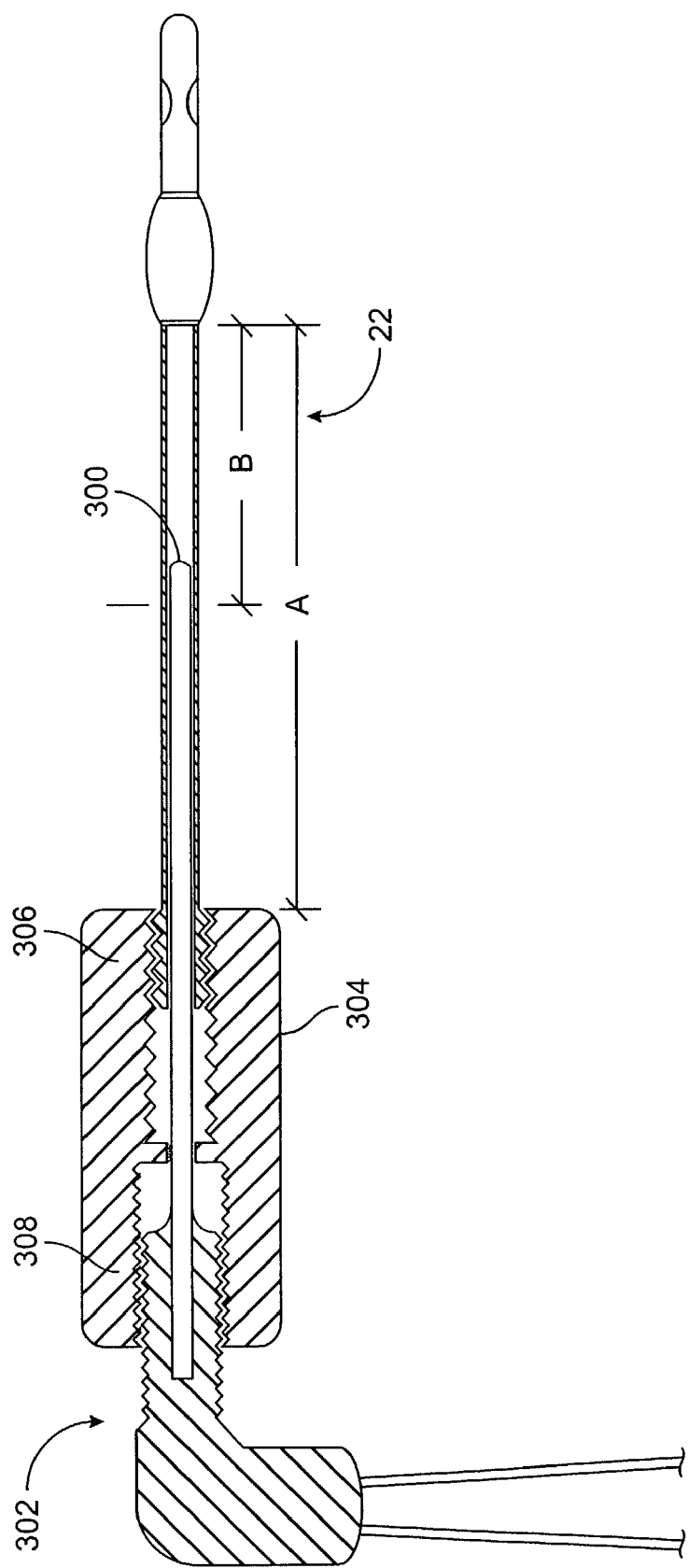
FIG. 24A to 24C illustrates another embodiment of a method and device for automatically locating the mid-urethral position and placing a sensor or other position indicating device at the mid-urethra.
Figure 24B:
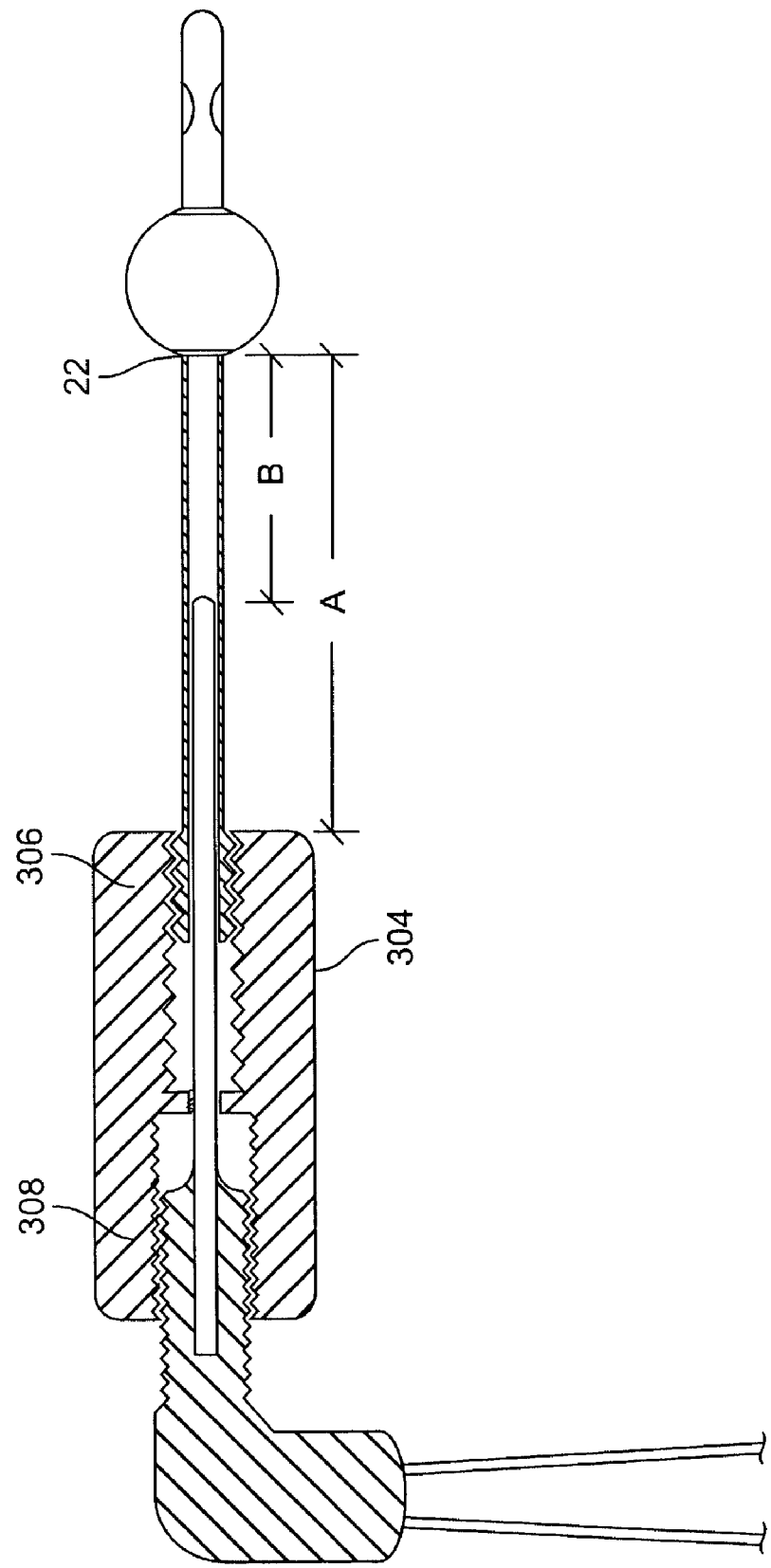
Figure 24C:
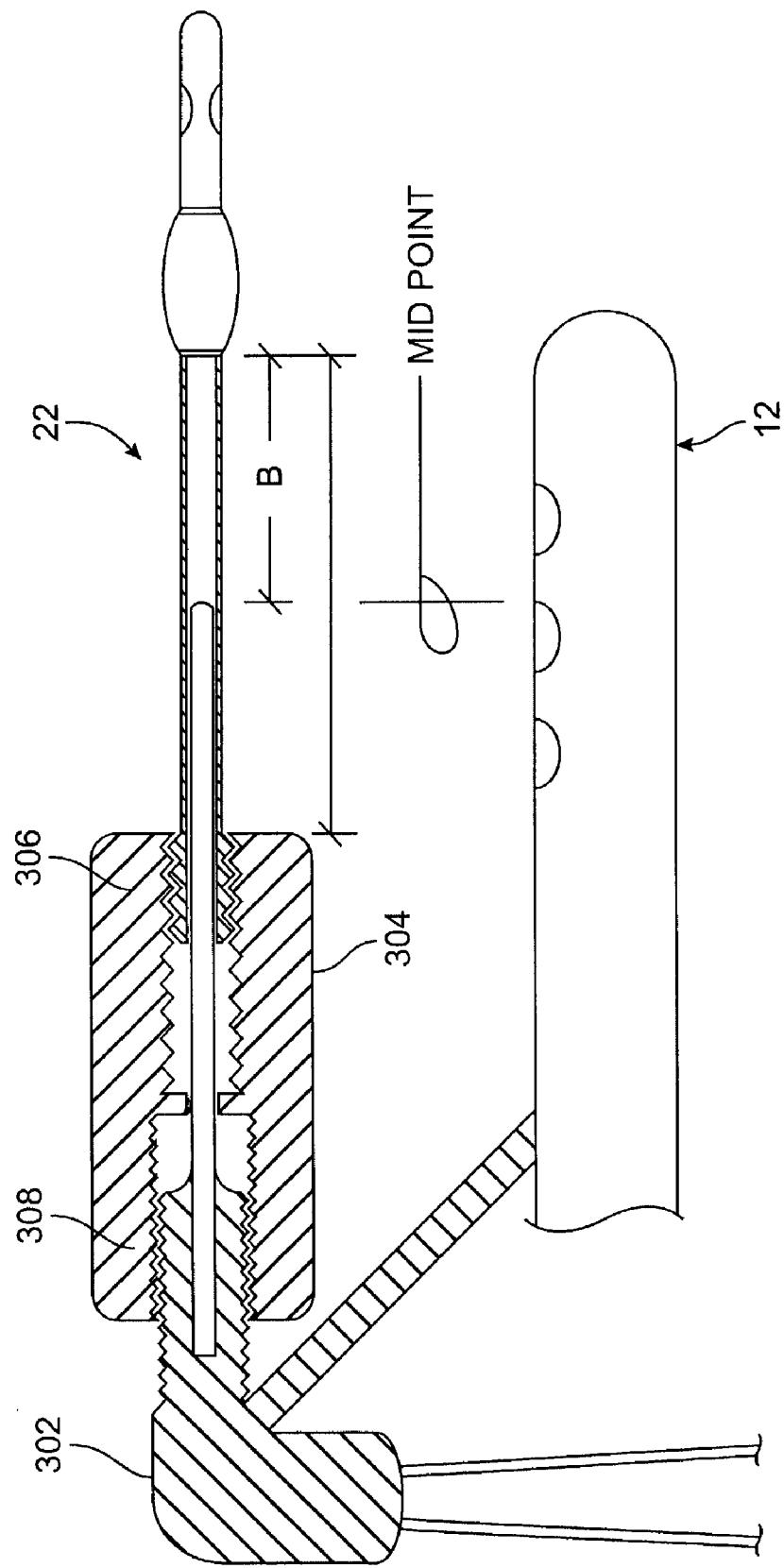

In another embodiment, the methods and device illustrated in FIGS. 24A to 24C can be used to automatically place a sensor or palpation device at the mid urethra position once the device is adjusted to equal the total length A of the patient's urethra. As shown in FIG. 24A, urethral guide 22 can include a movable marker 300 such as an RF/magnetic transmitter or receiver, or an expansion member disposed within a lumen of urethral guide 22 that is coupled to a rotating adjustment assembly 304. A stationary proximal body 302 can be coupled to the urethral guide 22 via the rotating adjustment assembly 304. In the illustrated embodiment, the position of the marker 300 can move as the adjustment assembly is rotated and moved axially and will always be positioned at a half-way point B of the distance A.

In the illustrated embodiment, a proximal end of urethral guide 22 can include a 2X-pitch screw thread 306 and a distal end of proximal body 302 can include fine pitch screws that have an X-fine pitch screw threads 308. Thus, in the illustrated embodiments in FIGS. 24B and 24C, the urethral guide 22 can be inserted into the urethra and the adjustment assembly 304 is rotated and moved into contact against the urethra meatus, such that the length between the balloon and the distal end of the adjustment assembly will be equal to A which is then equal to the patients urethral length. The marker 300 can maintain its center position at the mid-urethra point B due to the 2:1 pitch difference of the threads 306, 308 and the sensor or transmitter on the probe body 12 can be positioned adjacent the mid-urethra point, as described above. Thereafter, the probe body 12 can be inserted into the patient's vagina and positioned adjacent the target tissue, using any of the above recited methods.

Figure 25:
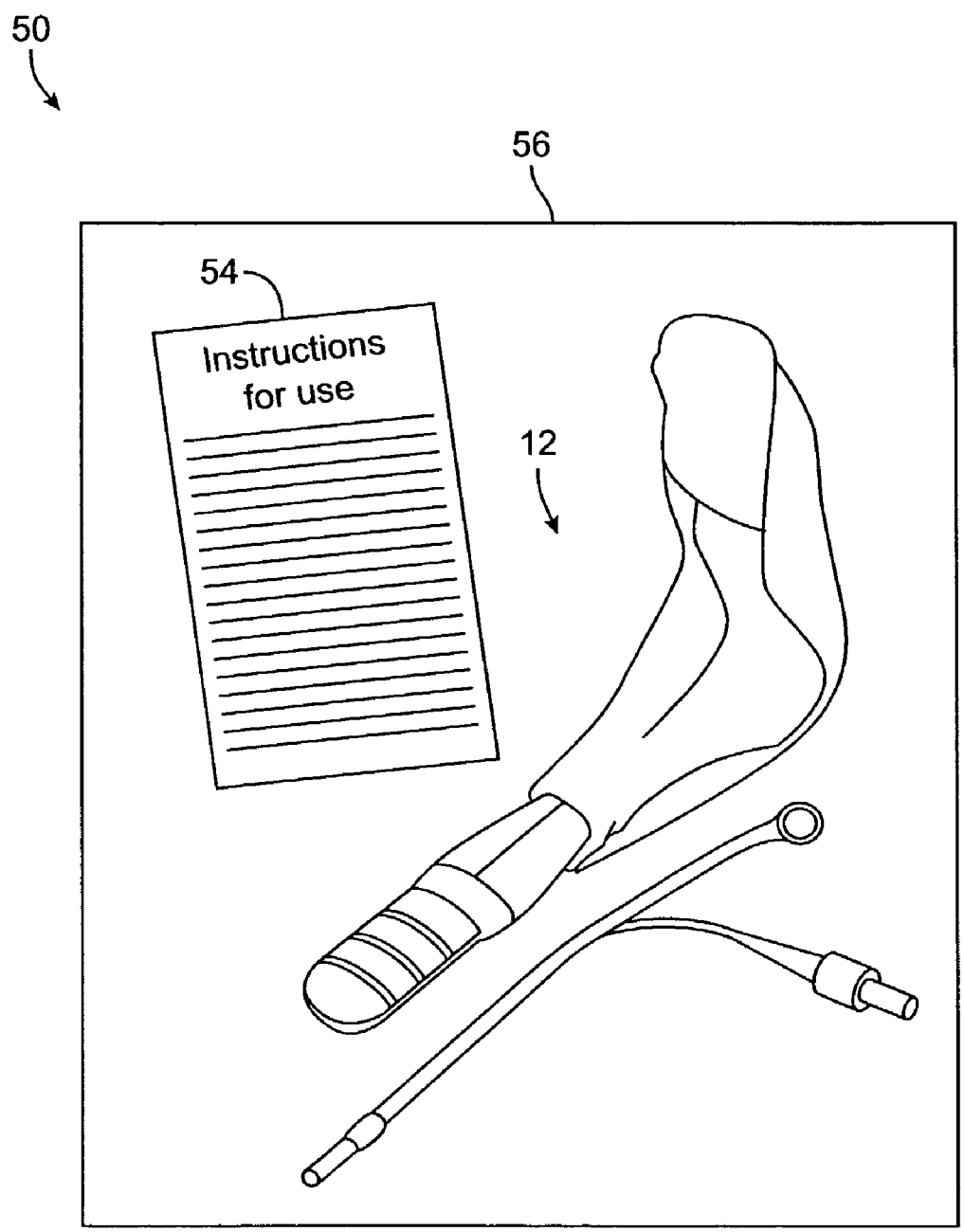
FIG. 25 illustrates an embodiment of a kit of the present invention.

Referring now to FIG. 25, a kit 50 includes a probe 12, a guide 22 and instructions for use 54. Probe 12, guide 22, and instructions 54 can be placed in packaging 56. Guide 22 can be any of the embodiments described above, and instructions 54 can set forth the steps of one or more of the methods described herein for heating and shrinking or stiffening tissue for treating urinary incontinence. Additional elements of the above described systems may also be included in packaging 56, or may alternatively be packaged separately.

Instructions 54 will often comprise printed material, and may also be found in whole or in part on packaging 56. Alternatively, instructions may be in the form of a recording disk, CD-ROM or other computer-readable medium, video tape, sound recording, or the like.

While the above is a complete description of the preferred embodiments of the inventions, various alternatives, modifications, and equivalents may be used. For example, it may be possible to make the angular offset of the urethral guide adjustable, laterally from the probe body and/or orthogonal to a plane of the electrode. Moreover, instead of inserting the guide and probe in different body orifices, in alternative uses, both the guide and probe may be inserted in the same body orifice. Although the foregoing has been described in detail for purposes of clarity of understanding, it will be obvious that certain modifications may be practiced within the scope of the appended claim.

What is claimed is:

1. A probe comprising:
    a guide that is configured to be inserted into a urethra; and
    a probe body comprising a treatment surface that is configured to be inserted into a vagina and placed in a predetermined non-parallel angular offset position relative to the guide so as to position the treatment surface adjacent a target tissue in the second body orifice.

2. The probe of claim 1 wherein the predetermined position has the guide and probe body spaced from each other.

3. The probe of claim 1 wherein the probe body is placed in the predetermined position relative to the guide using an RF coupling assembly.

4. The probe of claim 3 wherein the RF coupling assembly comprises at least one RF sensor on one of the guide and probe body and at least one RF transmitter on the other of the guide and probe body.

5. The probe of claim 1 wherein the probe body is placed in the predetermined position relative to the guide using a magnetic coupling assembly.

6. The probe of claim 5 wherein the magnetic coupling assembly comprises at least one electromagnetic source on one of the guide and probe body and at least one electromagnetic sensor on the other of the guide and probe body.

7. The probe of claim 6 wherein the electromagnetic sensor comprises a Hall effect sensor.

8. The probe of claim 1 wherein the probe body comprises two opposed palpation members that are adjacent and spaced from the treatment surface.

9. The probe of claim 8 wherein the guide comprises:
    a tubular member comprising a proximal end and a distal end;
    an expansion device on the tubular member that creates an expanded region at a predetermined point of the tubular member.

10. The probe of claim 9 wherein the expansion device comprises an elongate shaft comprising an expansion member, wherein the elongate shaft is movably disposed with a lumen of the tubular member, wherein movement of the expansion member to the predetermined point of the elongate shaft causes the tubular member at the predetermined point to expand from a first width to a second, larger width.

11. The probe of claim 10 wherein the predetermined point is approximately a halfway point between the proximal and distal ends.

12. The probe of claim 8 further comprising a clip that comprises a palpation member on a distal portion, wherein the clip is attachable to the guide so as to position the clip palpation member at a predetermined point in the second body orifice.

13. The probe of claim 1 wherein in the predetermined position the probe body is physically coupled to the guide.

14. The probe of claim 13 wherein the guide comprises a proximal portion, a distal portion, and a longitudinal axis, wherein the predetermined position relative to the guide positions a longitudinal axis of the probe body at an angled orientation relative to the longitudinal axis of the guide.

15. The probe of claim 14 wherein longitudinal axis of the guide is angled between approximately 5 degrees and 30 degrees from the longitudinal axis of the probe body.

16. The probe of claim 13 wherein the guide is removably attachable to the probe body.

17. The probe of claim 13 wherein the treatment surface defines a plane, wherein a top surface of the guide is positioned below the plane, wherein insertion of the guide into the first orifice biases the treatment surface against the target tissue.

18. The probe of claim 13 wherein the guide and probe body are coupled in a rigid configuration.

19. The probe of claim 1 wherein the guide comprises an expansible distal end.

20. The probe of claim 19 wherein the guide comprises an inflation lumen coupled to the expansible distal end.

21. The probe of claim 19 wherein the expansible end in an expanded configuration is adapted to be positioned in a patient's bladder to lock the guide in place.

22. The probe of claim 1 wherein the guide comprises a distal opening and a fluid lumen for draining fluid from a patient's bladder.

23. The probe of claim 1 wherein the guide comprises means for measuring a length of the first body orifice and means for determining an approximate midpoint of a first body lumen.

24. The probe of claim 1 wherein a distal end of the guide extends distally beyond a distal end of the probe body when the probe body is in the predetermined position.

25. The probe of claim 1 wherein the treatment surface comprises a plurality of electrode surfaces.

26. The probe of claim 1 wherein at least one of the probe body and guide comprise a temperature sensor.

27. A probe for treating a target tissue, the probe comprising:
    a probe body comprising a treatment surface, wherein the probe body is configured to be inserted into a body orifice; and
    guide means that are registerable with the probe body for positioning the treatment surface adjacent the target tissue, wherein the guide means are configured to be inserted into a different body orifice;
    wherein the guide means is maintained at a non-parallel, angular offset from the probe body.

28. The probe of claim 27 wherein the body orifice is a vagina and the different body orifice is an urethra.

29. A method for treating a target tissue, the method comprising:
    placing a guide into a first body orifice;
    inserting a probe comprising a treatment surface into a second body orifice;
    registering the probe with the guide to position the treatment surface adjacent the target tissue, wherein the guide is maintained at a non-parallel, angular offset relative to the probe body; and
    treating the target tissue with the treatment surface.

30. The method of claim 29 further comprising measuring a length of the first body orifice, wherein placing the guide into the first body orifice comprises advancing the guide into the first body orifice a predetermined distance.

31. The method of claim 30 wherein the predetermined distance is approximately half of the length of the second body orifice.

32. The method of claim 29 wherein the first body orifice is an urethra and the second body orifice is a vagina.

33. The method of claim 29 wherein placing and inserting are carried out independently.

34. The method of claim 29 wherein inserting and placing are carried out simultaneously.

35. The method of claim 29 wherein registering comprises coupling the probe to the guide.

36. The method of claim 35 wherein coupling comprises attaching the guide in an offset non-parallel, angular alignment with the probe.

37. The method of claim 36 wherein in the non-parallel, angular offset alignment a longitudinal axis of the guide and a longitudinal axis of the probe are at an angle between an angle of approximately 5 degrees and 30 degrees.

38. The method of claim 35 wherein coupling comprises biasing the treatment surface against the target tissue.

39. The method of claim 35 further comprising tensioning tissue adjacent the guide.

40. The method of claim 35 further comprising restraining the distal position of the probe.

41. The method of claim 35 wherein coupling comprises laterally offsetting the probe from urethral tissue towards an endopelvic fascia tissue.

42. The method of claim 29 further comprising locking the guide in the first body orifice.

43. The method of claim 42 wherein locking comprises inflating an expansible member on the guide.

44. The method of claim 43 further comprising draining fluid from the first body orifice.

45. The method of claim 29 wherein treating comprises heating the target tissue.

46. The method of claim 29 wherein registering the probe with the guide comprises positioning the probe relative to the guide using a RF coupling assembly.

47. The method of claim 46 comprising providing at least one RF transmitter on one of the guide and probe and at least one RF sensor on the other of the guide and probe.

48. The method of claim 29 wherein registering the probe with the guide comprises positioning the probe relative to the guide using an electromagnetic coupling assembly.

49. The method of claim 48 comprising providing at least one electromagnetic transmitter on one of the guide and probe and at least one electromagnetic sensor on the other of the guide and probe.

50. The method of claim 29 wherein registering comprises: creating a marker in the second orifice adjacent the target tissue; and aligning a marker on the probe with the marker in the second orifice.

51. The method of claim 50 wherein creating the marker comprises forming a bump in a wall of the second orifice.

52. The method of claim 50 wherein creating a marker comprises attaching a clip to the guide and inserting the clip in the second orifice.

53. A method of positioning a treatment surface adjacent a target tissue, the method comprising:
measuring a length of a patient's urethra;
inserting a urethral guide in the patient's urethra a predetermined distance;
inserting a vaginal probe comprising the treatment surface in a vagina;
positioning the probe and guide in a predetermined alignment, wherein the predetermined alignment positions the treatment surface adjacent the target tissue.

54. The method of claim 53, wherein the treatment surface comprises an electrode(s), and further comprising shrinking or stiffening the target tissue, wherein the shrinking or stiffening the target tissue treats incontinence.

55. The method of claim 53 wherein the predetermined distance is approximately half a length of the patient's urethra.

56. The method of claim 53 wherein inserting the urethral guide in the patient's urethra a predetermined distance is carried out automatically.

57. The method of claim 53 wherein measuring the length of the patient's urethra comprises manually measuring a length of the urethra.

58. The method of claim 53 wherein positioning the probe and guide in a predetermined alignment comprises coupling the guide and probe together.

59. The method of claim 58 wherein coupling comprises biasing the vaginal probe against the target tissue.

60. The method of claim 53 further comprising maintaining the position of the urethral guide in the urethra.

61. The method of claim 60 wherein maintaining comprises expanding an expansible member of the urethral guide in a bladder.

62. A kit comprising:
a probe body comprising a treatment surface;
a guide configured to be positioned in a non-parallel offset position relative to the probe body; and
an attachment structure for attaching the guide to the probe, wherein said attachment structure is configured to maintain a non-parallel, angular offset configuration between the guide and the probe.

63. The kit of claim 62 wherein the treatment surfaces comprises at least one electrode.

64. The kit of claim 63 further comprising a power source that is attachable to the at least one electrode.

65. A kit comprising:
a probe body comprising a treatment surface; and
a guide configured to be positioned in a non-parallel offset position relative to the probe body;
wherein one of the guide and probe comprises at least one RF transmitter and the other of the guide and probe comprises at least one RF sensor.

66. A kit comprising:
a probe body comprising a treatment surface; and
a guide configured to be positioned in a non-parallel offset position relative to the probe body;
wherein one of the guide and probe comprise at least one electromagnetic source and the other of the guide and probe comprise at least one electromagnetic sensor.

67. A kit comprising:
a probe body comprising a treatment surface; and
a guide configured to be positioned in a non-parallel offset position relative to the probe body;
wherein the guide comprises means for measuring a length of the first body orifice and means for measuring a midpoint of the first body orifice.

68. The probe of claim 1 wherein the probe body is placed in the predetermined position relative to the guide using an electromagnetic coupling assembly.

69. The probe of claim 13 wherein the guide is rotatably attached to the probe about at least one axis.

70. The probe of claim 69 wherein the guide is maintained at least at a minimum angular offset from the probe body.

71. The method of claim 29 wherein registering comprises rotatably coupling the guide to the probe.

72. The method of claim 71 comprising allowing rotation about at least one degree of rotation.

73. The method of claim 71 comprising allowing rotation about a plurality of degrees of rotation.

74. A probe comprising:
a guide that is configured to be inserted into a first body orifice; and
a probe body comprising a treatment surface that is configured to be inserted into a second body orifice and placed in a predetermined position relative to the guide using an electromagnetic coupling assembly that comprises at least one transmitter on one of the guide and the probe body and at least one receiver on the other of the probe body and guide so as to position the treatment surface adjacent a target tissue in the second body orifice.

75. The probe of claim 74, wherein the electromagnetic coupling assembly is an RF coupling assembly.

76. The probe of claim 74 wherein the RF coupling assembly comprises at least one RF sensor on one of the guide and probe body and at least one RF transmitter on the other of the guide and probe body.

77. The probe of claim 74, wherein the electromagnetic coupling assembly is a magnetic coupling assembly.

78. The probe of claim 77, wherein the magnetic coupling assembly comprises at least one electromagnetic source on one of the guide and probe body and at least one electromagnetic sensor on the other of the guide and probe body.

79. A method for treating a target tissue, the method comprising:

placing a guide into a first body orifice;

inserting a probe comprising a treatment surface into a second body orifice;

registering the probe with the guide to position the treatment surface adjacent the target tissue, wherein registering the probe with the guide comprises positioning the probe relative to the guide using an electromagnetic coupling assembly that comprises at least one transmitter on one of the guide and the probe body and at least one receiver on the other of the probe body and guide.

80. The method of claim 79, wherein the electromagnetic coupling assembly is an RF coupling assembly.

81. The method of claim 80 comprising providing at least one RF transmitter on one of the guide and probe and at least one RF sensor on the other of the guide and probe.

82. The method of claim 79, wherein the electromagnetic coupling assembly is a magnetic coupling assembly.

83. The method of claim 82, wherein the magnetic coupling assembly comprises at least one electromagnetic source on one of the guide and probe body and at least one electromagnetic sensor on the other of the guide and probe body.

* * * * *

UNITED STATES PATENT AND TRADEMARK OFFICE
CERTIFICATE OF CORRECTION

| | | |
|---|---|---|
| PATENT NO. | : 7,052,453 B2 | |
| APPLICATION NO. | : 10/301561 | |
| DATED | : May 30, 2006 | |
| INVENTOR(S) | : James B. Presthus et al. | |

It is certified that error appears in the above-identified patent and that said Letters Patent is hereby corrected as shown below:

On the Title Page, item (73) Assignee: "Solorant" should be -- Solarant --.

In Claim 44, column 17, line 18, "43" should be -- 29 --.

Signed and Sealed this
Twelfth Day of April, 2011

David J. Kappos
*Director of the United States Patent and Trademark Office*